(12) United States Patent
Kovalcheck et al.

(10) Patent No.: US 7,824,870 B2
(45) Date of Patent: Nov. 2, 2010

(54) SYSTEM FOR DISSOCIATION AND REMOVAL OF PROTEINACEOUS TISSUE

(75) Inventors: Steven W. Kovalcheck, Aliso Viejo, CA (US); John C. Huculak, Mission Viejo, CA (US)

(73) Assignee: Alcon, Inc., Hunenberg (CH)

( * ) Notice: Subject to any disclaimer, the term of this patent is extended or adjusted under 35 U.S.C. 154(b) by 692 days.

(21) Appl. No.: 11/608,877

(22) Filed: Dec. 11, 2006

(65) Prior Publication Data

US 2007/0156129 A1 Jul. 5, 2007

Related U.S. Application Data

(60) Provisional application No. 60/755,839, filed on Jan. 3, 2006.

(51) Int. Cl.
| | |
|---|---|
| C12N 13/00 | (2006.01) |
| C12M 1/00 | (2006.01) |
| C12M 3/00 | (2006.01) |
| A61F 2/00 | (2006.01) |
| A61F 9/007 | (2006.01) |
| A61N 1/32 | (2006.01) |

(52) U.S. Cl. ............ 435/7.21; 435/173.1; 435/283.1; 435/285.2; 435/286.1; 424/427; 607/96; 607/98; 607/115

(58) Field of Classification Search ............ None
See application file for complete search history.

(56) References Cited

U.S. PATENT DOCUMENTS

| | | | |
|---|---|---|---|
| 4,597,388 A | 7/1986 | Koziol et al. | |
| 5,869,326 A | 2/1999 | Hofmann | |
| 5,871,469 A | 2/1999 | Eggers et al. | |
| 5,925,045 A | 7/1999 | Reimels et al. | |
| 6,135,998 A | 10/2000 | Palanker | |
| 6,326,177 B1 | 12/2001 | Schoenbach et al. | |
| 6,479,785 B1 | 11/2002 | Fugo et al. | |
| 6,620,160 B2 | 9/2003 | Lewis et al. | |
| 6,632,193 B1 | 10/2003 | Davison et al. | |
| 6,653,114 B2 | 11/2003 | Walters et al. | |
| 6,730,075 B2 | 5/2004 | Palanker et al. | |
| 6,746,613 B2 | 6/2004 | Korenev | |
| 6,773,736 B1 | 8/2004 | De Winter et al. | |
| 6,780,178 B2 | 8/2004 | Palanker et al. | |
| 6,795,728 B2 | 9/2004 | Chornenky et al. | |
| 6,855,143 B2 | 2/2005 | Davison et al. | |
| 6,881,317 B2 | 4/2005 | Huang et al. | |
| 6,937,890 B2 | 8/2005 | Jaroszeski et al. | |
| 6,994,706 B2 | 2/2006 | Chornenky et al. | |
| 7,011,790 B2 | 3/2006 | Ruan et al. | |
| 7,037,694 B2 | 5/2006 | Aksenov et al. | |
| 7,053,063 B2 | 5/2006 | Rubinsky et al. | |
| 7,054,685 B2 | 5/2006 | Dimmer et al. | |
| 7,059,269 B2 | 6/2006 | Korenev | |
| 7,146,210 B2 | 12/2006 | Palti et al. | |
| 7,171,264 B1 | 1/2007 | Hofmann et al. | |
| 7,173,211 B2 | 2/2007 | Coccio et al. | |
| 7,182,762 B2 | 2/2007 | Bortkiewicz et al. | |
| 7,211,083 B2 | 5/2007 | Chornenky et al. | |
| 7,217,268 B2 | 5/2007 | Eggers et al. | |
| 7,220,261 B2 | 5/2007 | Truckai et al. | |
| 7,267,676 B2 | 9/2007 | Chornenky et al. | |
| 7,316,682 B2 | 1/2008 | Konesky et al. | |
| 7,338,656 B2 | 3/2008 | Draghia-Akli et al. | |
| 7,357,802 B2 | 4/2008 | Palanker et al. | |
| 7,395,110 B2 | 7/2008 | Hofman | |
| 7,419,575 B2 | 9/2008 | Culberston et al. | |
| 7,429,262 B2 | 9/2008 | Woloszko et al. | |
| 7,435,247 B2 | 10/2008 | Woloszko et al. | |
| 7,445,618 B2 | 11/2008 | Eggers et al. | |
| 2001/0037106 A1 | 11/2001 | Shadduck | |
| 2002/0062126 A1 | 5/2002 | Lewis et al. | |
| 2002/0095147 A1 | 7/2002 | Shadduck | |
| 2003/0208200 A1 | 11/2003 | Palanker et al. | |
| 2004/0176713 A1 | 9/2004 | Garth et al. | |
| 2004/0186466 A1 | 9/2004 | Chornenky et al. | |
| 2004/0193097 A1 | 9/2004 | Hofmann et al. | |
| 2004/0219660 A1 | 11/2004 | Dev et al. | |
| 2004/0236321 A1 | 11/2004 | Palanker et al. | |
| 2005/0161331 A1 | 7/2005 | Huang et al. | |
| 2005/0171523 A1 | 8/2005 | Rubinsky et al. | |
| 2005/0209548 A1 | 9/2005 | Dev et al. | |
| 2005/0211638 A1 | 9/2005 | Schrive et al. | |
| 2005/0220674 A1 | 10/2005 | Shafirstein et al. | |
| 2006/0028145 A1 | 2/2006 | Mohamed | |
| 2006/0041277 A1 | 2/2006 | Deem et al. | |
| 2006/0062074 A1 | 3/2006 | Gundersen et al. | |
| 2006/0041277 A1 | 2/2006 | Deem et al. | |
| 2006/0062074 A1 | 3/2006 | Gundersen et al. | |

(Continued)

FOREIGN PATENT DOCUMENTS

| | | |
|---|---|---|
| DE | 19740530 | 3/1999 |
| DE | 19740530 A1 | 3/1999 |
| WO | 0110319 A1 | 2/2001 |
| WO | WO 01/10319 | 2/2001 |
| WO | WO 2005/125287 A2 | 12/2005 |
| WO | WO 2005012587 A2 | 12/2005 |

OTHER PUBLICATIONS

Chen, M-T, et al "Two-dimensional nanosecond cell electropermeabilization" PMC Biophysics, 2009, (2(9), 16 pages.*

(Continued)

*Primary Examiner*—Christopher R Tate
*Assistant Examiner*—Aaron J Kosar
(74) *Attorney, Agent, or Firm*—Kenneth D. Bassinger

(57) ABSTRACT

An apparatus and method for the dissociation of soft proteinaceous tissue using pulsed rapid variable direction energy field flow fractionization is disclosed. The pulsed rapid disruptive energy field is created by the use of a probe which surrounds the soft proteinaceous tissue to be removed. Once the adhesive mechanism between tissue constituents has been compromised, fluidic techniques are used to remove the dissociated tissue.

21 Claims, 18 Drawing Sheets

U.S. PATENT DOCUMENTS

| | | |
|---|---|---|
| 2006/0089674 A1 | 4/2006 | Walters et al. |
| 2006/0118485 A1 | 6/2006 | Gallagher |
| 2006/0127271 A1 | 6/2006 | Ruan |
| 2006/0141555 A1 | 6/2006 | Knowles |
| 2006/0224192 A1 | 10/2006 | Dimmer |
| 2006/0264805 A1 | 11/2006 | Singh |
| 2006/0265015 A1 | 11/2006 | Demarais |
| 2006/0269531 A1 | 11/2006 | Beebe |
| 2006/0271111 A1 | 11/2006 | Demarais |
| 2006/0276852 A1 | 12/2006 | Damarais |
| 2006/0293713 A1 | 12/2006 | Rubinsky |
| 2006/0293725 A1 | 12/2006 | Rubinsky |
| 2006/0293730 A1 | 12/2006 | Rubinsky |
| 2006/0293731 A1 | 12/2006 | Rubinsky |
| 2007/0029500 A1 | 2/2007 | Coulombe |
| 2007/0059835 A1 | 3/2007 | Chalberg et al. |
| 2007/0129761 A1 | 6/2007 | Demarais et al. |
| 2007/0135875 A1 | 6/2007 | Demarais et al. |
| 2007/0179535 A1 | 8/2007 | Morrissey et al. |
| 2007/0219118 A1 | 9/2007 | Lu et al. |
| 2007/0265215 A1 | 11/2007 | Iversen et al. |
| 2008/0027428 A1 | 1/2008 | Palanker et al. |
| 2008/0039832 A1 | 2/2008 | Palanker et al. |
| 2008/0039901 A1 | 2/2008 | Kronberg et al. |
| 2008/0045941 A1 | 2/2008 | Fugo |
| 2008/0099406 A1 | 5/2008 | Ruan et al. |
| 2008/0119842 A1 | 5/2008 | Palanker et al. |
| 2008/0125774 A1 | 5/2008 | Palanker et al. |
| 2008/0167645 A1 | 7/2008 | Woloszko et al. |
| 2008/0188846 A1 | 8/2008 | Palanker et al. |
| 2008/0200912 A1 | 8/2008 | Long |
| 2008/0228244 A1 | 9/2008 | Pakhomov et al. |
| 2008/0231337 A1 | 9/2008 | Krishnaswamy et al. |
| 2008/0241315 A1 | 10/2008 | Kalum et al. |
| 2008/0269586 A1 | 10/2008 | Rubinsky et al. |

OTHER PUBLICATIONS

Sanders, J.M., et al "A Linear, Single-stage, Nanosecond Pulse Generator for Delivering Intense Electric Fields to Biological Loads" IEEE Transactions on Dielectrics and Electrical Insulation, Aug. 2009, 16(4), pp. 1048-1054.*

Gundersen, M. A., M. R. Behrend, Y. Sun, P. T. Vernier, and A. Kuthi, "Four-channel pulse generator for real-time biological investigations," Proc. 26th International Power Modulator Symposium and 2004 High Voltage Workshop, 2004, abstract 67, pp. 210-215.*

Daniel V. Palanker, Alexander Vankov, and Philip Huie; "Electrosurgery with Cellular Precision"; IEEE Transactions on Biomedical Engineering, vol. 55, No. 2; Feb. 2, 2008; pp. 838-841.

Heinz V., Alvarez I., Angersbacha A. and Knorra D.; "Preservation of Liquid Foods By High Intensity Pulsed Electric Fields—Basic Concepts For Process Design"; Trends in Food Science & Technology 12 (2002) pp. 103-111.

Taijisakamoto Y., Hisatomi T., Tsutsumi C., Sassa Y., Ishibashi T. and Inomata H.; "Targeted Gene Transfer to Corneal Stroma in Vivo by Electric Pulse"; Experimental Eye Research (2002) 74, pp. 191-198.

Dezawaa M., Takanob M., Negishic H., Moc X., Oshitaric T. and Sawadaa H.; "Gene Transfer Into Retinal Ganglion Cells By In Vivo Electroporation: A New Approach"; Micron 33 (2002); pp. 1-6.

Heeren T., Ueno T., Wang D., Namihira T., Katsuki S., and Akiyama H.; "Novel Duel Marx Generator for Microplasma Applications"; Plasma Science, IEEE Transactions on vol. 33, Issue 4, Aug. 2005; pp. 1205-1209.

Schoenbach KH, Nuccitelli R. and Beebe SJ; "Zap—Extreme Voltage Could Be A Surprisingly Delicate Tool In The Fight Against Cancer"; EEE Spectrum, Aug. 2006; pp. 20-26.

Behrend MR., Sun Y., Vernier PT, Kuthi A., and Gundersen MA; "Four-Channel Pulse Generator For Real-Time Biological Investigations"; Abstract 67 Proc. IEEE Int'l Power Modulator Symposium, 2004, pp. 210-215.

Zhang L. and Rabussay DP; "Clinical Evaluation of Safety and Human Tolerance of Electrical Sensation Induced by Electric Fields With Non-Invasive Electrodes"; Bioelectrochemistry 56 (2002); pp. 233-236.

Bennett DJ., Khusid B., James CD, Galambos PC, and Okandan M.; "Combined Field-Induced Dielectrophoresis and Phase Separation For Manipulating Particles in Microfluidics"; Applied Physics Letter vol. 83, No. 23 Dec. 8, 2003; pp. 4866-4868.

Faurie C., Golzio M., Phex E., Teissie J. and Rols MP; "Electirc Field-Induced Cell Membrane Permeabilization and Gene Transfer: Theorory and Experiments"; Eng Life Sci 2005, 5, No. 2 pp. 179-186.

Priglinger SG, Haritoglou C., Mueller A., Grueterich M., Strauss RW., Alge CS, Gandorfer A., Palanker D. and Kampik A.; "Pulsed Electron Avalanche Knife in Vitreoretinal Surgery"; Retina 2005 vol. 25, No. 7, pp. 889-896.

Miller L., Leor J., and Rubinsky B.; "Cancer Cells Ablation With Irreversible Electroporation"; Technology in Cancer Research & Treatment, vol. 4, No. 5, pp. 699-705, Dec. 2005.

Davalos RV., Mir LM, and Rubinsky B.; "Tissue Ablation With Irreversible Electroporation"; Annals of Biomedical Engineering; vol. 33: No. 2: pp. 223-231, Feb. 2005.

Kolb JF., Kono S., and Schoenbach KH; "Nanosecond Pulsed Electric Field Generators For the Study of Subcellular Effects"; Bioelectromagnetics 27:127-187 (2006); pp. 172-187.

Chen Z. and Chauhan A.; "Electrochemical Response and Separation in Cycle Electric Field-Flow Fractionation"; Electrophoresis 2007, 28, pp. 724-739.

Bejjani R.A., Andrieu C., Bloquel C., Berdugo M., Benezra D., and Behar-Cohen F.; "Electrically Assisted Ocular Gene Therapy"; Survey of Ophthalmology vol. 52, No. 2, Mar.-Apr. 2007; pp. 196-208.

Garon E., Sawcer D., Vernier T., Tang T., Sun Y., Marcu L., Gundersen M. and Koeffler H.; "In Vitro and In Vivo Evaluation and a Case Report of Intense Nanosecond Pulsed Electric Field as a Local Therapy for Huma Malignancies"; Internation Journal of Cancer, 121, pp. 675-682 (2007).

Priglinger S., Haritoglou C., Palanker D., Kook D., Grueterich M., Mueller A., Alge C. and Kampik A.; "Pulsed Electron Avalanche Knife for Capsulotomy in Congenital and Mature Cataract"; J. Cataract and Refractive Surgery 32, Jul. 2006; pp. 1085-1088.

Fox M., Esveld D. and Boom R.; "Conceptual Design Of A Mass Parallelized PEF Microreactor:"; Trends in Food Science & Technology 18 (2007) pp. 484-491.

Vankov A. and Palanker D.; "Nanosecond Plasma-Mediated Electrosurgery with Elongated Electrodes"; Journal of Applied Physics 101, 124701 (2007).

Priglinger S., Hartiglou C., Palanker D., Alge C., Gandorfer A., and Kampik A.; "Pulsed Electron Avanche Knife (PEAK-fc) For Dissection of Retinal Tissue"; Arch Ophthalmol vol. 123, Oct. 2005, pp. 1412-1418.

Prigliner S., Palanker D., Alge C., Kreutzer T., Haritoglou C., Grueterich M. and Kampik A.; "Pulsed Electron Avalanche Knife: New Technology For Cataract Surgery"; Br. J. Ophthalmol 2007, 91: Nos. 949-954.

Katsuki S., Nomura N., Koga H. and Akiyama H.; "Biological Effects of Narrow Band Pulsed Electric Fields"; IEEE Transaction on Dielectrics and Electrical Insulation, vol. 14, No. 3: Jun. 2007; pp. 663-668.

Fridman G., Shereshevsky A., Peddinghauys M., Gutsol A., Vasilets V., Brooks A., Balasubramanian M., Friedman G. and Fridman 1.; "Bio-Medical Applications of Non-Thermal Atmospheric Pressure Plasma"; 37th AIAA Plasmadynamics and Lasers Conference Jun. 5-8, 2006, San Francisco, CA, 5 pages.

Fridman G., Brooks A., Balasubramanian M., Freidman A., Gustol A., Vasilets V., Ayan H. and Friedman G.; "Comparison of Direct and Indirect Effects of Non-Thermal Atmospheric-Pressure Plasma on Bacteria"; Plasma Process and Polymers 2007, 4, pgs. 370-375.

Sarkar P., Novac B., Smith I. and Miller R.; "A High-Repetition Rate Closing Switch for EMP Applications", Pulsed Power Conf., 2007 16th IEEE Int'l, Jun. 2007, vol. 1, pp. 97-100.

Oblak J., Krizaj D., Amon S., Macek-Lebar A. and Miklavcic D.; "Feasibility Study For Cell Electroporation Detection and Separation by Means of Dielectrophoresis"; Bioelectrochemistry 71, (2007), pp. 164-171.

Chen N., Garner A., Chen G., Jing Y., Deng Y., Swanson R., Kolb J., Beebe S. Joshi R and Schoenbach K.; "Nanosecond Electric Pulses Penetrate the Nucleus and Enhance Speckle Formation"; Biochemical and Biophysical Research Communications 364 (2007), pp. 220-225.

Chen X., Yao C., Li C., Sun C., Mi Y., Li C. and Hu L.; "Frequency Response Model and Simulation of Transmembrane Potentials on Cellular Inner and Outer Membranes"; Proceedings of the 29th Annual International Conference of the IEEE EMBS Cite Internationale, Lyon, France Aug. 23-26, 2007; pp. 5818-5821.

Shiina S., Ohshima T. and Sato M., "Extracellular Release of Recombinant r-Amylase From *Escherichia coli* Using Pulsed Electric Field"; Biotechnol. Prog. 2004, 20, pp. 1528-1533.

Krishnaswamy P., Kuthi A., Vernier P. and Gundersen M.; "Compact Subnanosecond Pulse Generator Using Avalanche Transistors For Cell Electroperturbation Studies"; IEEE Transactions on Dielectrics and Electrical Insulation vol. 14, No. 4; Aug. 2007; pp. 871-877.

Koners U., Schmidt W., Loffler M., Heinz V. and Knorr D.; "The Effect of Implemented Pulsed Electric Field (PEF) Treatment on the Dehydrogenase Activity of Activated Slugde"; WIT Transactions on Ecology and the Environment, vol. 95, 2006; pp. 379-388.

Fox M., Esveld D., Mastwijk H. and Boom R.; "Inactivation of L. Plantarum in a PEF Microreactor the Effect of Pulse Width and Temperature on the Inactivaton"; Innovative Food Science and Emerging Technolagies 9 (2008). pp. 101-108.

Zaharoff D., Henshaw J., Mossop B. and Yuan F.; "Mechanistic Analysis of Electroporation-Induced Cellular Uptake of Macromolecules"; Exp Biol Med 233: pp. 94-105, 2008.

Zhang J., Blackmore P., Hargrave B., Xiao S., Beebe S. and Schoenbach K.; "Nanosecond Pulse Electric Field (Nanopulse): A Novel Non-Ligand Agonist For Platelet Activation"; Archives of Biochemistry and Biophysics 471 (2008) pp. 240-248.

Lin C., Wang J. and Fu L.; "Improving the Separation Efficiency of DNA Biosamples in Capillary-Electrophoresis Microchips Using High-Voltage Pulsed DC Electric Fields"; Microfluid Nanofluid DOI 10.1007/s10404-008-0259-7, 2008, 5 (3), pp. 403-410.

Sato M., Ohgiyama T. and Clements JS.; "Formation of Chemical Species and Their Effects on Microorganisms Using a Pulsed High Voltage Discharge in Water"; 0-7803-1993-1/91 1994 IEEE; pp. 1455-1461.

Sato M., Ohgiyama T. and Clements JS.; "Formation of Chemical Species and Their Effects on Microorganisms Using a Pulsed High Voltage Discharge in Water"; IEEE Transactions on Industry Applications vol. 32, No. 1, Jan./Feb. 1996; pp. 106-112.

Vernier P.T., Sun Y., Chen. M.T., Gundersen M.A. and Craviso G.L.; "Nanosecond Electric Pulse-Induced Calcium Entry Into Chromaffin Cells"; Bioelectrochemistry 73 (2008) 1-4.

Kono S., Ono T., Hirayama K., Matsushita K., Katsuki S. and Akiyqmq H.; "Biological Effects of Pulsed Electric Field by Several Ways of Applying Voltage"; 0-7803-9189-6/05/$20.00 © C2005 IEEE; pp. 1425-1428.

Gaudreau M., Hawkey T., Petry J. and Kempkes M.; Solid-State Power Systems for Pulsed Electric Field (PEF) Processing; 0-7803-9189-6/05/05/$20.00© 2005 IEEE; pp. 1278-1281.

Uchida S., Houjo M. and Tochikubo F.; "Efficient Sterilization of Bacteria by Pulse Electric Field in Micro-Gap"; Journal of Electrostatics 66 (2008) pp. 427-431.

Song G., Qin J., Yao C. and Ju Y.; "Effect of Steep Pulsed Electric Field on Proliferation, Viscoelasticity and Adhesion of Human Hepatoma SMMC-7721 Celis"; Anticancer Research 28:2245-2252 (2008).

Min S., Evrendilek G.A. and Zhang H.Q.; "Pulsed Electric Fields: Processing System, Microbial and Enzyme Inhibition, and Shelf Life Extension of Foods"; IEEE Transactions on Plasma Science, vol. 35, No. 1, Feb. 2007, pp. 59-73.

Kishore N.K., Emani S.S., Maiti T.K. and Bisht G.S.; "Studies on Pulsed Electric Field Applications for Food Sterilization"; 2nd Intern Conf on Industrial and Information Systems, ICIIS 2007, Aug. 8-11, 2007, Sri Lanka.

Nuccitelli R., Pliquett U., Chen X., Ford W., Swanson R.J., Beebe S.J., Kolb J.F. and Schoenbach K.H.; "Nanosecond Pulsed Electric Fields Cause Melanomas to Self-Destruct";Biochemical and Biophysical Research Communications 343 (2006) pp. 351-360.

Thurston G.B. and Gaertner E.B.; "Viscoelasticity of Electrorheological Fluids During Oscillatory Flow in a Rectangular Channel"; Journal of Rheology, vol. 35 (7), pp. 1327-1343, Oct. 1991.

Palanker D.V., Vankov A., Bilbao K., Marmor M. and Blumenkranz M.S.; "Optimization of The Pulsed Electron Avalanche Knife For Anterior Segment Surgery"; Proc. SPIE vol, 4951, p. 56-61, Ophthalmic Technologies XIII; Jul 2003 (CD 4951-10).

Woloszko J., Kwende M. and Stalder K.R.; "Coblation in Otolaryngology"; Proc. SPIE vol. 4949, p. 341-352, Lasers in Surgery: Advanced Characterization, Therapeutics, and Systems XIII; Jun. 2003 (See CD 4949-55).

Woloszko J. and Gilbride C.; "Coblation Technology: Plasma-Mediated Ablation For Otolaryngology Applications"; Proc. SPIE vol. 3907, p. 306-316, Lasers in Surgery: Advanced Characterization, Therapeutics, and Systems X; May 2000.

Sebag J. and Hageman G.S.; "Interfaces"; European Journal Of Ophthalmology vol. 10, Issue 1, Jan.-Mar. 2000, pp. 1-3.

Palanker D.V., Miller J.M., Marmor M.F., Sanisto S.R., Huie P., Blumenkranz M.S.; "Pulsed Electron Avalanche Knife (PEAK) for Intraocular Surgery"; Invest Ophthal & Vis Science, vol. 42 (11), pp. 2673-2678, Oct. 2001.

Schoenbach, K.H., Joshi R.P., Kolb J.F., Chen N. Stacey, M., Blackmore P.F., Buescher E.S., Beebe S.J.; "Ultrashort Electrical Pulses Open a New Gateway Into Biological Cells"; Proceedings of the IEEE, 92 (7), pp. 1122-1137, Jul. 2004.

Hofmann G.A.; "Instrumentation and Electrodes For In Vivo Electroporation"; Methods in Molecular Medicine vol. 37, Ch. 2, pp. 37-61, 2000.

Stoffels E., Kief I.E., Sladek E.J., Van Der Lann E.P. and Slaaf W.; "Gas Plasma Treatment: A New Approach to Surgery?"; Minicourse 2004 ICOPS (IEEE).

Kim H.B., Ahu S., and Sim S.B.; "Apoptosis by Direct Electric Field (DEF) and Nanosecond Pulsed Electric Field (nsPEF) in Tumor Cells and Tumor Tissues"; ICOPS 2003, 7A01-02, p. 436.

Stalder, K.R., Woloszko J., Brown I.G., and Smith C.D.; "Repetitive Plasma Discharges in Saline Solutions"; Appl. Phys. Lett. 79(27) 4503 (Dec. 13, 2001).

Stalder K.R. and Woloszko J.; "Electrosurgical Plasma Discharges"; Am Phys Society—55th Gaseous Electronic Conference HT2.003 Oct. 2002.

Deng J., Schoenbach K.H., Buescher E.S., and Hair P.S.; "The Effects of Intense Submicrosecond Electrical Pulses on Cells"; Biophysical Journal, vol. 84, pp. 2709-2714, 2003.

Stalder K.R.; "Plasma Characteristics of Electrosurgical Discharges"; Am Physical Sac, Gaseous Electronics Conference, ET1. 002, Oct. 2003.

Stoffels E., et al.; "Plasma Needle: A Non-Destructive Atmospheric Plasma Source For Fine Surface Treatment of (Bio)Materials"; Plasma Sources Sci Technol, 11, 383-388 (2002).

Stoffels E., et al.; Superficial Treatment of Mammalian Cells Using Plasma Needle; Phys. D: Appl. Phys. 36, 2908-2913 (2003).

Williams G. and Thomas D.K.; "Phenomenological and Molecular Theories of Dielectric and Electrical Relaxation of Materials"; Nonoconlrol GmbH. Application Note Dielectric 3 (1998).

Teague B.D, Wemyss-Holden S.A., Fosh B.G., Dennison A.R. and Maddern G.J.; "Electrolysis and Other Local Ablative Treatments for Non-Resectable Colorectal Liver Metastases"; ANZ-Journal-of-Surgery; 2002; 72/2 (137-141).

Joshi R.P., Hu Q., Schoenbach K.H., and Beebe S.J.; "Energy-Landscape-Model Analysis of Irreversibility and Its Pulse-Width Dependence in Cells Subjected to High Intensity Ultrashort Electric Pulse"; Physical Review E 69, 051901-1, 2004.

White J.A., Blackmore P.F., Schoenbach K.H. and Beebe S.J.; "Stimulation of Capacitive Calcium Entry in HL-60 Cells by Nanosecond Pulsed Electric Fields"; Journal of Biological Chemistry, vol. 279 (22), pp. 22964-22972.

Gaudet J.A., Buchenauer C.J., Dickens J., Joshi R.P., Kolb J.F., Neuber A., Schamiloglu E., and Tyo J.S.; "Research Issues in Developing Compact Pulsed Power for High Peak Power Applications on Mobile Platforms"; Proceedings of the IEEE, vol. 92 (7), pp. 1144-1165, Jul. 2004.

Schoenbach K.H., Joshi R.P., Kolb J.F., Chen N., Stacey M., Blackmore P.F., Buescher E.S. and Beebe S.J.; "Ultrashort Electrical Pulses Open a New Gateway Into Biological Cells"; Proceedings of the IEEE, vol. 92 (7), pp. 1122-1137, Jul. 2004.

Pakhomov A.G., Phinney A., Anshmore J., Walker K., Kolb J. and Kono S.; "Characterization of the Cytotoxic Effect of High-Intensity, 10-ns. Duration Electrical Pulses"; TPS0419.R1, US Army Medical Research DAMD 17-94-C-4069, Oct. 2003.

Beebe S.J., White J., Blackmore P.F., Deng Y., Somers K., and Schoenbach K.H.; "Diverse Effects of Nanosecond Pulsed Electric Fields on Cells and Tissues"; DNA and Cell Biology, vol. 22 (12), 2003.

Chen N., Schoenbach K.H., Kolb J F., Swanson R.J., Garner A.L., Yang J., Joshi R.P., and Beebe S.J.; "Leukemic Cell Intracellular Responses to Nanosecond Electric Fields"; Biochemical and Biophysical Research Communications 317 (2004) pp. 421-427.

Stacey M., Stickley J., Fox P., Statler V., Schoenbach K., Beebe S.J. and Buescher S.; "Differential Effects in Cells Exposed to Ultra-Short, High Intensity Electric Fields: Cell Survival, DNA Damage, and Cell Cycle Analysis"; Mutation Research 542 (2003) pp. 65-75.

Joshi R.P., Hu Q. and Schoenbach K.H.; "Dynamical Modeling of Cellular Response to Short-Duration, High-Intensity Electric Fields"; IEEE Tansactions on Dielectrics and Electrical Insulation, vol. 10 (5), Oct. 2003, pp. 778-787.

Buescher E.S. and Schoenbach K.H.; "Effects of Submicrosecond, High Intensity Pulsed Electric Fields on Living Cells-Intracellular Electromanipulation"; IEEE Transactions on Dielectrics and Electrical Insulation, vol. 10 (5), Oct. 2003, pp. 788-794.

Beebe S.J., Fox P.M., Rec L.J.; Willis L.K. and Schoenbach K.H.; "Nanosecond, High-Intensity Pulsed Electric Fields Induce Apoptosis in Human Cells"; FASEB Journal, Express Article 10, 1098/fj.02-0859fje. Published online Jun. 17, 2003.

Deng J., Schoenbach K.H., Buescher E.S., and Hair P.S.; "The Effects of Intense Submicrosecond Electrical Pluses on Cells"; Biophysical Journal, vol. 84, pp. 2709-2714, Apr. 2003.

Hair P.S., Schoenbach K.H. and Buescher E.S.; "Sub-Microsecond, Intense Pulsed Electric Field Applications to Cells Show Specificity of Effects"; Bioelectrochemistry, vol. 61, pp. 65-72, 2003.

Block H. and Kelly J.P.; "Electro-Rheology Review Article"; J. Phys. D: Appl. Phys. 21 1661-1677, 1988.

Ikazaki F., Kawai A., Uchida K., Kawakami K.T., Edamura K., Sakurai K., Anza H. and Asako Y.; "Mechanisms of Electrorheology: The Effects of the Dielectric Property"; J. Phys. D: Appl. Phys. 31 336-347, 1998.

Matthews J.A., Wnek G.E., Simpson D.G, and Bowlin G.L.; "Electrospinning of Collagen Nanofibers"; Biomacromolecules. Mar.-Apr. 2002; 3 (2): 232-8.

Binhi V.N., and Goldman R.J.; "Ion-Protein Dissociation Predicts 'Windows' In Electric Field-Induced Wound-Cell Proliferation"; Biochim-Biophys-Acta. Apr. 6, 2000; 1474(2): 147-56.

Fukada E.; "Electrical Phenomena in Biorheology"; Biorheology. 1982; 19(1/2): 15-27.

Puzas, J.E., Vignery A. and Rasmussen H.; "Isolation of Specific Bone Cell Types by Free-Flow Electrophoresis"; Calcified Tissue International. Jul. 3, 1979; 27(3): 263-8.

Behrend M., Kuthi A., Gu X., Vernie G.P., Marcu L. Craft C.M. and Gundersen M.A.; "Pulse Generators of Pulsed Electric Field Exposures of Biological Cells and Tissues"; IEEE Trans on Dielectrics and Electrical Insulation, vol. 10, No. 5, pp. 820-825, Oct. 2003.

Deng J., Stark R.H. and Schoenbach K.H.; "A Nanosecond Pulse Generator for Intracellular Electromanipulation"; 24th International Power Modulation Symposium, pp. 47-50, 2000.

Polk C., "Biological Applications of Large Electric Fields: Some History and Fundamentals"; IEEE Transactions on Plasma Science, vol. 28 (1), pp. 6-14 Feb. 2000.

Rosche S., "Solid State Pulsed Power Systems"; (White Paper); Physique & Industrie, 17 Run de la Rente Logerot, 21160 Marsannay La Cote, France.

Wijetunga P., Gu X., Vernier P.T., Kuthi A., Behrend M. and Gundersen M.A.; "Electrical Modeling of Pulsed Power Systems for Biomedical Applications"; Abstract No. #10324 Preprint mag@usc.edu.

Mankowski J. and Kristiansen M.; "A Reivew of Short Pulse Generator Technology"; IEEE Transactions on Plasma Science, vol. 28 (1), pp. 102-108 Feb. 2000.

Xiao S., Kolb J., Kono S., Katsuki S., Joshi R.P., Laroussi M. and Schoenback K.H,; "High Power, High Recovery Rate Water Switch"; Abstract #10672 Preprint.

Sampayan S., Caporaso G., Carder B., Chen Y., Holmes C., Lauer E., and Trimble D.; "High Gradient Insulator Technology for the Dielectric Wall Accelerator"; US Depart of Energy, Lawrence Livermore National Laboratory contract No. W-7405-Eng-48.

Van Heesch E.J.M., Pemen A.J.M., Huigbrechts A.H.J., Van Der Lanna P.C.T., Ptasinski K.J., Zanstra G.J. and De Jong P.; "A Fast Pulsed Power Source Applied to Treatment of Conducting Liquids and Air"; IEEE Transactions on Plasma Science, vol. 28 (1), Feb. 2000.

Lu X.P., Laroussi M., Kolb J., Kono S., and Schoenbach K.H.; "Temporal Emission Behavior of Pulsed Discharge in Water"; Reprint.

Tyo J.S., Skipper M.C., Abdalla M.D., Romero S.P. and Cockreham B.; "Frequency and Bandwidth Agile Pulser for Use in Wideband Applications"; IEEE Transactions on Plasma Science, Pulsed Power Technology Jan. 2004.

Kolb J., Kono S., Xiao S., Goan B., Lu X.P., Bickes C., Laroussi M., Joshi R.P., Schoenbach K. and Schamiloglu E.; "Water and Propylene Carbonate as Storage and Switching Media in Pulsed Power Systems"; Abstract No. #10699 Preprint.

Kuthi A., Young C., Wang F., Wijetunga P. and Gundersen M.; "Rapid Charger for High Repetition Rate Pulse Generator"; Abstract No. #10320 Preprint.

Miller J.M, Palanker D.V., Vankov A., Marmor M.F., and Blumenkranz M.S.; "Precision and Safety of the Pulsed Electron Avalanche Knife in Vitreoretinal Surgery", Arch Ophthalmology, vol. 121, pp. 871-877, Jun. 2003.

Grekhov I., Korotkov S., Stepaniants A., Khristyuk D. and Voronkov V.; "High Power Semiconductor-Based Nano and Subnanosecond Pulse Generator with A Low Delay Time"; Loffe Institute RAS, 26 Poytekhicheskaya, St. Peterburg, 194021, Russia.

Han J. and Singh A.K.; "Rapid Protein Separations in Ultra-Short Mlcrochannels: Microchip Sodium Dodecyl Sulfate-Polyacrylamide Gel Electrophoresis and Isoelectric Focusing"; Journal of Chromatography A, vol. 1049 (1-2), Sep. 2004, pp. 205-209.

Bazant M.Z. and Squires T.M.; "Induced-Charge Electrokinetic Phenomena: Theory and Microfluidic Applications"; Physical Review Letters, vol. 92 (6), pp. 066101-1 to 066101-4, Feb. 2004.

Squires T.M. and Bazant M.Z.; "Induced-Charge Electro-Osmosis"; J. Fluid Mechanics vol. 509, pp. 217-252, 2004.

Lin M.P., Marti G.P., Dieb R., Wang J., Qaiser R., Bonde P., Duncan M.D. and Harmon J.W.; "Electroporation Improves Transfection Efficiency in Rat Wound Healing Model"; J. American College of Surgeons, vol. 199 (3), Supp 1, Sep. 2004, pp. 58-59.

Laroussi M., "Biological Decontamination by Non-Equilibrium Plasmas: High Pressure Case"; Minicourse, ICOPS 2004, Baltimore, MA.

Lao Aik, Tra D., and Hsing IM; "Miniaturized Flow Fractionation Device Assisted by a Pulsed Electric Field for Nanoparticle Separation"; Anal. Chem, vol. 74, pp. 5364-5369, 2002.

Palanker D.V., Marmor M.F., Branco A., Huie P., Miller J.M., Sanislo S.R., Vankov A., and Blumenkranz M.S.; "Effects of Pulsed Electron Avalanche Knife on Retinal Tissue"; Arch Ophthalmol, vol. 120, pp. 636-640, 2002.

Garner H. Hofman, GA, Dev S.B. and Nanda G.S.; "Electrochemotherapy: Transition from Laboratory to the Clinic"; Engineering in Medicine and Biology Magazine, IEEE, vol. 15 (6), pp. 124-132, Nov.-Dec. 1996.

Vernier P.T., Li A., Marcu L., Craft C.M. and Gundersen M.A.; "Ultrashort Pulsed Electric Fields Induce Membrane Phospholipid Translocation and Caspase Activation: Differential Sensitivities of Jurkat T. Lymphoblasts and Rat Glioma C6 Cells"; IEEE Transactions on Dielectrics and Electrical Insulatiion vol. 10, No. 5; Oct. 2003 795.

Kuthia A., Behrend M., Vernier T., and Gundersen M.; "Bipolar Nanosecond Pulse Generation Using Transmission Lines for Cell Electro-Manipulation", Proc. 26th Int'l Power Modulator Symposium and 2004 High Voltage Workshop, pp. 224-227, 2004.

Sata M., Ohgiyama T. and Clements J.S.; "Formation of Chemical Species and Their Effects on Microorganisms Using a Pulsed High-Voltage Discharge in Water"; IEEE Trans on Indust Appl, vol. 32 (1), Jan./Feb. 1996.

O'Malley C. and Heintz R.M.; "Electrovitreotomy"; Am J. Opthalmol. 76(3), pp. 336-342, Sep. 1973.

O'Malley C. and Heintz R.M.; Electrovitreotomy, 2. Principals and Results; Br. J. Ophthalmol, 59 (10), pp. 580-585, Oct. 1975.

Reschiglian P., Zattoni A., Roda B., Michelini E., and Roda A.; "Field-Flow Fractionation and Biotechnology"; Trends in Biotechnology vol. 23 (9), p. 475-483, Sep. 2005.

Nuccitelli R., Pliquett U., Chen X., Ford W., Swanson R.J., Beebe S.J., Kolb J.F., and Schoenbach K.H.; "Nanosecond Pulsed Electric Fields Cause Melanomas to Self-Destruct"; Biochemical and Biophysical Research Commuications, vol. 343 (2), pp. 351-360, May 2006.

Schrive L., Grasmick A., Moussiere S., Sarrade S.; "Pulsed Electric Field Treatment of Saccharomyces Cerevisiae Suspensions: A Mechanistic Approach Coupling Energy Transfer, Mass Transfer and Hydrodynamics"; Biochemical Engineering, Journal 27 (2006) 212-224.

Focia R.J. and Frost C.A.; "A Compact, Low Jitter, 1 Khz Pulse Repetition Rate Gasswitched Pulse Generator System"; Preprint of 2005 Pulsed Power Conference Paper, 4 pages.

Chalemchat Y., Dejmek P.; "Effects of Pulsed Electric Field Pretreatment on Solid-Liquid Expression From Potato Tissue"; Journal of Food Engineering 71 (2005) 164-169.

Jayaram S.H., El-Hag A.H. Espino-Cortes F.P., Wong R.J. and Leibovitch C.; "Effects of Process and Product Parameters on The Shape of Nanosecond Pulses Used in High-Field Liquid Food Treatment"; IEEE Transactions on Industry Applications, vol. 41, No. 2, Mar./Apr. 2005.

Sek S., Swiatek K., and Misicka A.; "Electrical Behavior of Molecular Junctions Incorporating r-Helical"; Journal of Physical Chemistry B 2005, 109, 23121-23124 Nov. 17, 2005.

Hall E.H., Schoenbach K.H. and Beebe S.J.; "Nanosecond Pulsed Electric Fields (nsPEF) Induce Direct Electric Field Effects and Biological Effects on Human Colon Carcinoma Cells"; DNA and Cell Biology vol. 24, No. 5, 2005, pp. 283-291.

Chen Z. and Chauhan A.; "Separation of Charged Colloids By A Combination of Pulsating Lateral Electric Fields and Poiseuille Flow in A 2D Channel"; Journal of Colloid and Interface Science 282 (2005) 212-222.

Coa J.G., Huang J.P., and Zhou L.W.; "Structure of Electrorheological Fluids Under an Electric Field and a Shear Flow: Experiment and Computer Simulation"; J. Phys. Chem B2006, 100, 11635-11639.

Kolb J.F.; Kono S.; Schoenbach K.H.; "Nanosecond Pulsed Electric Field Generators For The Study of Subcellular Effects"; Bioelectromagnetics. Apr. 2006; 27(3): 172-87.

Mahrour N., Pologea-Moraru R., Moisescu M.G., Orlowski S., Leveque P., and Mir L.M.; "In Vitro Increase of The Fluid-Phase Endocytosis Induced by Pulsed Radiofrequency Electromagnetic Fields: Importance of The Electric Field Component"; Biochim-Biophys-Acta. Feb. 1, 2005; 1668(1): 126-37.

Udayan K. Shah, MD; "Coblation for Tonsillectomy in Children: An Evidence-Based Update on Maturing Technology"; Proc. SPIE, vol. 6424, p. 64241H1-64241H-12 (2007); doi: 10.1117/12.702641; Photonic Therapeutics and Diagnostics III.; Online Publication date Mar. 8, 2007.

Fridman G., Peddinghaus M., Ayan H., Fridman A., Balasubramanian M., Gutsol A., Brooks A., and Friedman G.; "Blood Coagulation and Living Tissue Sterilization by Floating-Electrode Dielectric Barrier Discharge in Air"; Plasma Chem Plasma Process: DOI 10.1007/s11090-006-9024-4. vol. 26, No. 4/ Aug. 2006; pp. 425-442.

Fridman G., Shereshevsky A., Jost M., Brooks A., Fridman A., Gustol A., Vasilets V., and Friedman G.; "Floating Electrode Dielectric Barrier Discharge Plasma in Air Promoting Apoptotic Behavior in Melanoma Skin Cancer Cell Lines"; Plasma Chem Plasma Process DOI 10.1007/s11090-007-9048-4; vol. 27, No. 2; Apr. 2007; pp. 163-176.

Hennig J.; "Diathermic Vitrectomy in Anterior Segment Surgery"; Advances in Vitreous Surgery: [1974: San Francisco Proceedings), edited by Irvine AR and O'Malley C. Springfield, Ill: Thomas, Published 1976; Chapter 42, pp. 463-467.

Gaudreau M., Hawkey T., Petry J., and Kempkes M.; "Solid State Power System for Pulsed Electric Field (PEF) Processing"; 2005 Proc IEEE Pulsed Power Conference; pp. 1278-1281.

Kono S., Ono T, Hirayama K., Matsushita K., Katsuki S., and Akiyama H.; "Biological Effects of Pulsed Electric Field by Several Ways of Applying Voltage"; 2005 Proc. IEEE Pulsed Power Conference, pp. 1425-1428.

Jayaram S.H. and Boggs S.A.; "Optimization of Electroporation Waveforms for Cell Sterilization"; 2004 Proc IEEE, on Industry Application vol. 40, pp. 1489-1497.

Alexander Vankov and Daniel Palanker; "Nanosecond Plasma-Mediated Electrosurgery With Elongated Electrodes"; Journal of Applied Physics 101; Published online Jun. 19, 2007; pp. 124701-124707.

V. Heinz, I. Alvarez, A. Angersbach, and D. Knorr; "Preservation of Liquid Foods by High Intensity Pulsed Electric Fields—Basic Concepts For Process Design"; Trends in Food Science & Technology 12 (2002); pp. 103-111.

Yuji Oshima, Taiji Sakamoto, Toshio Hisatomi, Chikako Tsutsumi, Yukio Sassa, Tatsuro Ishibashi, and Hajime Inomata; "Targeted Gene Transfer to Corneal Stroma In Vivo By Electric Pulses"; 2002 Elsevier Science Ltd.; pp. 191-198.

Mari Dezawa, Masahiko Takano, Hisanari Negishi, Xiaofen Mo, Toshiyuki Oshitari, and Hajime Sawada; "Gene Transfer Into Retinal Ganglion Cells By In Vivo Electroporation: A New Aproach"; Micron 33 (2002); pp. 1-6.

Tammo Heeren, Takahisa Ueno, Douyan Wang, Takao Namihira, Sunao Katsuki, and Hidenori Akiyama; "Noval Dual Marx Generator For Microplasma Applications"; IEEE Transactions on Plasma Science, vol. 33, No. 4 Aug. 2005; pp. 1205-1209.

Karl H. Schoenbach, Richard Nuccitelli and Stephen J. Beebe; "Zap—Extreme Voltage Could Be A Suprisingly Delicate Tool In The Fight Against Cancer"; IEEE Spectrum; Aug. 2006; pp. 20-26.

L. Zhang and D.P. Rabussay; "Clinical Evaluation of Safety and Human Tolerance of Electrical Sensation Induced by Electric Fields with Non-Invasive Electrodes"; Elsevier; Bioelectrochemisty 56 (2002); pp. 233-236.

Dawn J. Bennett, Boris Khusid, Conrad D. James, Paul C. Galambos, Murat Okandan, David Jacqmin, and Andreas Acrivos; "Combined Field-Induced Dielectrophoresis and Phase Separation For Manipulating Particles in Microfluidics"; Applied Physics Letters; vol. 83; No. 23; Dec. 8, 2003; pp. 4866-4868.

C. Faurie, M. Golzio, E Phez, J. Teissie, and M.P. Rols; "Electric Field-Induced Cell Membrane Permeabilization and Gene Transfer: Theory and Experiments"; Eng. Life Sci. 2005, 5, No. 2 pp. 179-186.

Siegfried G. Pringlinger, MD., Christos Haritoglou, MD., Arthur Mueller, MD., Martin Grueterich, MD., Rupert W. Strauss, MD., Claudia S. Alge, MD., Arnd Gandorfer, MD., Daniel Palanker PhD, and Anselm Kampik, MD.; "Pulsed Electron Avalanche Knife In Vitreoretinal Surgery"; Retina, The Journal of Retinal and Vitreous Diseases, 2005, vol. 25, No. 7, pp. 889-896.

Liron Miller, M.Sc., Jonathan Leor, MD., and Boris Rubinsky, PhD.; "Cancer Cells Ablation With Irreversible Electroporation"; Technology in Cancer Research & Treatment; ISSN 1533-0346; vol. 4, No. 6, Dec. 2005; pp. 699-705.

R.V. Davalos, L.M. Mir, and B. Rubinksy; "Tissue Ablation With Irreversible Electroporation"; Annals of Biomedical Engineering, vol. 33, No. 2, Feb. 2005; pp. 223-231.

Juergen F. Kolb, Susumu Kono, and Karl H. Schoenbach; "Nanosecond Pulsed Electric Field Generators For The Study of Subcellular Effects"; Bioelectromagnetics 27:172-187 (2006).

Zhi Chen and Anuj Chauhan; "Electrochemical Response and Separation In Cyclic Electric Field-Flow Fractionation"; Electrophoresis 2007, 28; pp. 724-739.

Riad Antoine Bejjani, MD., Charlotte Andrieu, PhD., Carole Bloquel, PhD., Marianne Berdugo, VetD, David Benezzra, MD., PhD, and Francine Behar-Cohen, MD., PhD.; Survey Of Ophthalmology; vol. 52, No. 2; Mar.-Apr. 2007; pp. 196-208.

Edward B. Garon, David Sawcer, P. Thomas Vernier, Tao Tang, Yinghua Sun, Laura Marcu, Martin A. Gundersen and H. Phillip Koeffler; "In Vitro and In Vivo Evaluation and A Case Report of Intense Nanosecond Pulsed Electric Field as a Local Therapy For Human Malignancies"; Int. J. Cancer; 121; pp. 675-682; (2007).

Siegfried G. Priglinger, MD., Christo Haritoglou, MD., Daniel Palanker, PhD., Daniel Kook, MD., Martin Grueterich, MD., Arthur Mueller, MD., Claudia S. Alge, MD., and Anselm Kampik, MD.; "Pulsed Electron Avalanche Knife For Capsulotomy in Congenital and Mature Cataract"; J Cataract Refract Surg, Jul. 2006; vol. 32, pp. 1085-1088.

Udayan K. Shah, MD.; "Coblation For Tonsillectomy in Children: An Evidence-Based Update on a Maturing Technology"; Proc. of SPIE, vol. 6424; pp. 64241 H-1 thru 64241H-12, 2007.

M.B. Fox, D.C. Esveld, and R.M. Boom; "Conceptual Design of a Mass Parallelized PEF Microreactor"; Trends in Food Science & Technology 18 (2007); pp. 484-491.

Siegfried G. Priglinger, MD., Christos Hartoglou, MD., Daniel V. Palanker, PhD., Claudia S. Alge, MD., Arnd Gandorfer, MD.; and Anselm Kampik, MD.; "Pulsed Electron Avalance Knife (PEAK-fc) for Dissection of Retinal Tissue"; Arch Ophthalmol Oct. 2005; vol. 123; pp. 1412-1418.

Siegfried G. Pringlinger, Daniel Palanker, Claudia S. Alge, Thomas C. Kreutzer, Christo Haritoglou, Martin Grueterich, and Anselm Kampik; "Pulsed Electron Avalanche Knife: New Technoloyg for Cataract Surgery"; Br J Ophthalmol; 2007; vol. 91; pp. 949-954.

Sunao Katsuki, Naoyuki Nomura, Hideto Koga, Hidenori Akiyama, Ichiro Uchida, and Shin-Ichi Abe; "Biological Effects of Narrow Band Pulsed Electric Fields"; IEEE Transactions on Dielectrics and Electrical Insulation; vol. 14, No. 3; Jun. 2007; pp. 663-668.

Gregory Fridman, Alexey Shereshevsky, Maria Peddinghaus, Alexander Gutsol, Victor Vasilets, Ari Brooks, Manjula Balasubramanian, Gary Friedman, and Alexander Fridman; "Bio-Medical Application of Non-Thermal Atmospheric Pressure Plasma"; 37th AIAA Plasmadynamics and Laser Conference Jun. 5-8, 2006, San Francisco CA., 5 pages.

Gregory Fridman, Marie Peddinghaus, Halim Ayan, Alexander Fridman, Manjula Balasubramanian, Alexander Gustol, Ari Brooks, and Gary Friedman; "Blood Coagulation and Living Tissue Sterilization by Floating-Electrode Dielectric Barrier Discharge in Air"; Plasma Chem Plasma Process; Feb. 2006, 18 pages.

Gregory Fridman, Alexey Shereshevsky, Monika M. Jost, Ari D. Brooks, Alexander Fridman, Alexander Gutsol, Victor Vasilets, and Gary Friedman; "Floating Electrode Dielectric Barrier Discharge Plasma in Air Promoting Apoptotic Behavior in Melanoma Skin Cancer Cell Lines"; Plasma Chem Plasma Process; Jan. 2007, 14 pages.

Gregory Fridman, Ari D. Brooks, Manjula Balasubramanian, Alexander Fridman, Alexander Gutsol, Victor N. Vasilets, Halim Ayan, and Gary Friedman; "Comparison of Direct and Indirect Effects of Non-Thermal Atmospheric-Pressure Plasma on Bacteria"; Plasma Processes and Polymers; 2007; vol. 4, pp. 370-375.

P. Sarkar, B.M. Novac, I.R. Smith, and R.A. Miller; "A High-Repetition Rate Closing Switch for EMP Applications";, IEEE 34th Intl conf 2007, 4 pages.

Jakob Oblak, Dejan Krizaj, Slavko Amon, Alenka Macek-Lebar, and Damijan Miklavcic; "Feasibility Study for Cell Electroporation Detection and Separation by Means of Dielectrophoresis"; ScienceDirect; Bioelectrochemistry 71 (2007); pp. 164-171.

Nianyong Chen, Allen L. Garner, George Chen, Yu Jing, Yuping Deng, R. James Swanson, Juergen F. Kolb, Stephen J. Beebe, Ravindra P. Joshi, and Karl H. Schoenbach; "Nanosecond Electric Pulses Penetrate the Nucleus and Enhance Speckle Formation"; ScienceDirect; Biochemical and Biophysical Research Communication 364 (2007); pp. 220-225.

Xin Chen, Chenguo Yao, Chengxiang Li, Caixin Sun, Yan Mi, Cong Li, Lina Hu; "Frequency Response Model and Simulation of Transmembrane Potentials on Cellular Inner and Outer Membranes"; Proceedings of the 29th Annual International Conference of the IEEE EMBS; Aug. 23-26, 2007; pp. 5818-5821.

Satoshi Shiina, Takayuki Ohshima, and Masayuki Sato; "Extracellular Release of Recombinant a-Amylase from *Escherichia coli* Using Pulsed Electric Field"; Biotechnol Prog. 2004, vol. 20, pp. 1528-1533.

Pavitra Krishnaswamy, Andras Kuthi, P. Thomas Vernier, and Martin A. Gundersen; "Compact Subnanosecond Pulse Generator Using Avalanche Transistors for Cell Electroperturbation Studies"; IEEE Transactions on Dielectrics and Electrical Insulation; vol. 14; No. 4; Aug. 2007; pp. 871-877.

U. Koners, W. Schmidt, M. Loffler, V. Heinz, and D. Knorr; "The Effect of Implemented Pulsed Electric Field (PEF) Treamtnet on the Dehydrogenase Activity of Activated Sludge"; WIT Transactions on Ecology and the Environment; vol. 95; 2006; pp. 379-388.

M.B. Fox, D.C. Esveld, H. Mastwijk, and R.M. Boom; "Inactivation of L. Plantarum in a PEF Microreactor The Effect of Pulse Width and Temperature on the Inactivation"; ScienceDirect; Innovative Food Science and Emerging Technologies; vol. 9; 2008; pp. 101-108.

David A. Zaharoff, Joshua W. Henshaw, Brian Mossop and Fan Yuan; "Mechanistic Analysis of Electroporation-Induced Cellular Uptake of Macromolecules"; Exp. Biol. 2008, 233, pp. 94-105.

Jue Zhang, Peter F. Blackmore, Barbara Y Hargrave, Shu Xiao, Stephen J. Beebe, and Karl H. Schoenbach; "Nanosecond Pulse Electric Field (Nanopulse): A Novel Non-Ligand Agonist for Platelet Activation"; ScienceDirect; Archives of Biochemistry and Biophysics; vol. 471; 2008; pp. 240-248.

Che-Hsin Lin; Jing-Hui Wang, and Lung-Ming Fu; "Improving the Separation Efficiency of DNA Biosamples in Capillary Electrophoresis Microchips Using High-Voltage Pulsed DC Electric Fields"; Microfluid Nanofluid;, 2008, 5, pp. 403-410.

Masayuki Sato, Takashi Ohgiyama, and J.S. Clements; "Formation of Chemical Species and Their Effects on Microorganisms Using a Pulsed High Voltage Discharge in Water"; IEEE; 1994; pp. 1455-1461.

Masayuki Sato, Takashi Ohgiyama, and J.S. Clements; "Formation of Chemical Species and Their Effects on Microorganisms Using a Pulsed High-Voltage Discharge in Water"; IEEE Transactions on Industry Applications; vol. 32, No. 1; Jan./Feb. 1996; pp. 106-112.

P. Thomas Vernier, Yinghua Sun, Meng-Tse Chen, Martin A. Gundersen, and Gale L. Craviso; "Nanosecond Electric Pulse-Induced Calcium Entry Into Chromaffin Cells"; Bioelectrochemisty 73; 2008; pp. 1-4.

S. Kono, T. Ono, K. Hirayama, and K. Matsushita; "Biological Effects of Pulsed Electric Field by Several Ways of Applying Voltage"; IEEE; 2005; pp. 1425-1428.

M. Gaudreau, T. Hawkey, J. Petry, and M. Kempkes; "Solid-State Power Systems for Pulsed Electric Field (PEF) Processing"; IEEE; 2005; pp. 1278-1281.

Satoshi Uchida, Makoto Houjo, and Fumiyoshi Tochikubo; "Efficient Sterilization of Bacteria by Pulse Electric Field in Micro-Gap"; Journal of Electrostatic 66 (2008); pp. 427-431.

Guanbin Song, Jian Qin, Chengguo Yao, and Yang Ju; "Effect of Steep Pulsed Electric Field on Proliferation, Viscoelasticity and Adhesion of Human Hepatoma SMMC-7721 Cells"; Anticancer Research 28; 2008; pp. 2245-2251.

Seacheol Min, Gulsun Akdemir Evrendilek, and Howard Q. Zhang; "Pulsed Electric Fields: Processing System, Microbial and Enzyme Inhibition, and Shelf Life Extension of Foods"; IEEE Transactions on Plasma Science, vol. 35; No. 1 Feb. 2007; pp. 59-73.

N. K. Kishore, Sriram Sarma Emani, T.K. Maiti, and Gobind Singh Bisht; "Studies on Pulsed Electric Field Applications for Food Sterilization"; Second International Conference on Industrial and Information Systems, ICIIS 2007, Aug. 8-11, 2007; pp. 497-502.

Richard Nuccitelli, Uwe Pliquett, Xinhua Chen, Wentia Ford, R. James Swanson, Stephen J. Beebe, Juergen F. Kolb, and Karl H. Schoenbach; "Nanosecond Pulsed Electric Fields Cause Melanomas to Self-Destruct"; ScienceDirect; Biochemical and Biophysical Research Communication 343; 2006; pp. 351-360.

\* cited by examiner

TABLE 5A

Activation scheme for embodiment in FIG. 4A

| Pulse | Anode (-) | Cathode (+) | Pulse | Anode (-) | Cathode (+) |
|---|---|---|---|---|---|
| 1 | 11 | 3, 4, 5 | 9 | 3, 4, 5 | 7, 8, 9 |
| 2 | 3. 4. 5 | 11 | 10 | 7, 8, 9 | 3, 4, 5 |
| 3 | 11 | 7, 8, 9 | 11 | 5, 6, 7 | 9, 10, 3 |
| 4 | 7, 8. 9 | 11 | 12 | 3, 10, 9 | 5, 6, 7 |
| 5 | 11 | 9, 10, 3 | | | |
| 6 | 9, 10, 3 | 11 | | | |
| 7 | 11 | 5, 6, 7 | | | |
| 8 | 5, 6, 7 | 11 | | | |

TABLE 5B
Activation scheme for embodiment in FIG. 4B

| Pulse | Anode (-) | Cathode (+) | Pulse | Anode (-) | Cathode (+) |
|---|---|---|---|---|---|
| 1 | 3, 4, 5 | 7, 8, 9 | 9 | 6, 8 | 4, 10 |
| 2 | 7, 8, 9 | 3. 4. 5 | 10 | 4, 6 | 8, 10 |
| 3 | 5, 6, 7 | 9, 10, 3 | 11 | 8, 10 | 4, 6 |
| 4 | 3, 5 | 7, 9 | | | |
| 5 | 7, 9 | 3, 5 | | | |
| 6 | 9, 3 | 5, 7 | | | |
| 7 | 5, 7 | 9,3 | | | |
| 8 | 4, 10 | 6, 8 | | | |

TABLE 5C

Activation scheme for embodiment in FIG. 4C

| Pulse | Anode (-) | Cathode (+) | Pulse | Anode (-) | Cathode (+) |
|---|---|---|---|---|---|
| 1 | 3, 4 | 11 | 9 | 3, 4 | 7, 8 |
| 2 | 11 | 3, 4 | 10 | 7, 8 | 3, 4 |
| 3 | 7, 8 | 11 | 11 | 5, 6 | 9, 10 |
| 4 | 11 | 7, 8 | 12 | 9, 10 | 5, 6 |
| 5 | 5, 6 | 11 | | | |
| 6 | 11 | 5, 6 | | | |
| 7 | 9, 10 | 11 | | | |
| 8 | 11 | 9, 10 | | | |

TABLE 5D

Activation scheme for embodiment in FIG. 4D

| Pulse | Anode (-) | Cathode (+) | Pulse | Anode (-) | Cathode (+) |
|---|---|---|---|---|---|
| 1 | 3, 4 | 11 | 9 | 6, 8 | 4 |
| 2 | 11 | 3. 4 | 10 | 4 | 6, 8 |
| 3 | 5, 6 | 11 | | | |
| 4 | 11 | 5, 6 | | | |
| 5 | 7, 8 | 11 | | | |
| 6 | 11 | 7, 8 | | | |
| 7 | 5, 7 | 3 | | | |
| 8 | 3 | 5, 7 | | | |

TABLE 5E

Activation scheme for embodiment in FIG. 4E

| Pulse | Anode (-) | Cathode (+) | Pulse | Anode (-) | Cathode (+) |
|-------|-----------|-------------|-------|-----------|-------------|
| 1 | 3, 4 | 12 | 9 | 6, 8 | 4 |
| 2 | 12 | 3, 4 | 10 | 4 | 6, 8 |
| 3 | 5, 6 | 12 | | | |
| 4 | 12 | 5, 6 | | | |
| 5 | 7, 8 | 12 | | | |
| 6 | 12 | 7, 8 | | | |
| 7 | 5, 7 | 3 | | | |
| 8 | 3 | 5, 7 | | | |

FIG. 11A
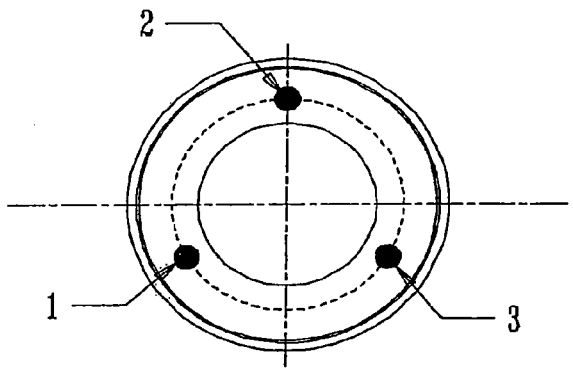
FIG. 12A
Activation scheme for embodiemtn of Figure 11A
| | Switching With Reverse Polarity | | | Switching Without Reverse Polarity | |
|---|---|---|---|---|---|
| Pulse | Anode (-) Electrodes | Cathode (+) Electrodes | Pulse | Anode (-) Electrodes | Cathode (+) Electrodes |
| 1 | 1 | 2, 3 | 1 | 1 | 2, 3 |
| 2 | 2, 3 | 1 | 2 | 2 | 1, 3 |
| 3 | 2 | 3, 1 | 3 | 3 | 1, 2 |
| 4 | 3, 1 | 2 | | | |
| 5 | 3 | 1, 2 | | | |
| 6 | 1, 2 | 3 | | | |
FIG. 13A
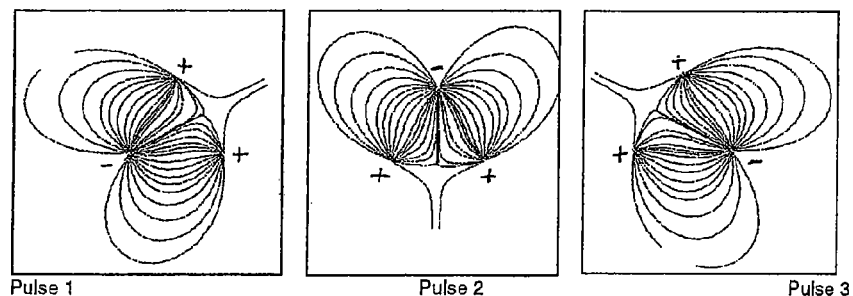
Pulse 1  Pulse 2  Pulse 3
FIGURE 13A ELECTRIC FIELD LINES FOR SEQUENCE OF TABLE 12A
NO REVERSING POLARITY

FIG. 11B

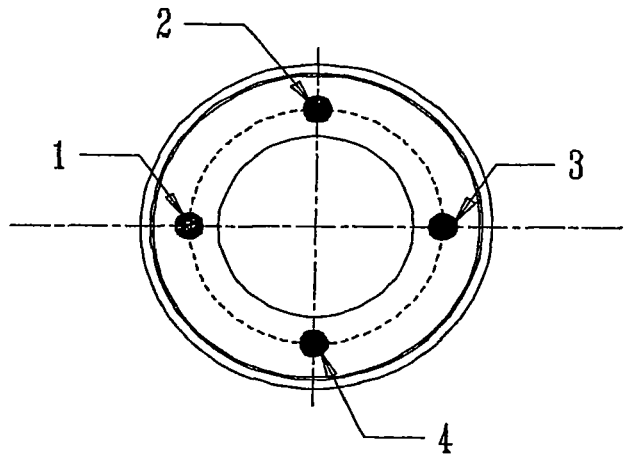

FIG. 12B

Activation scheme for embodiment in Figure 11B - electrodes activated in pairs

| | Switching With Reverse Polarity | | | Switching Without Reverse Polarity | |
|---|---|---|---|---|---|
| Pulse | Anode (-) Electrodes | Cathode (+) Electrodes | Pulse | Anode (-) Electrodes | Cathode (+) Electrodes |
| 1 | 1 and 2 | 3 and 4 | 1 | 1 and 2 | 3 and 4 |
| 2 | 3 and 4 | 1 and 2 | 2 | 2 and 3 | 4 and 1 |
| 3 | 2 and 3 | 4 and 1 | 3 | 3 and 4 | 1 and 2 |
| 4 | 4 and 1 | 2 and 3 | 4 | 4 and 1 | 2 and 3 |

FIG. 13B

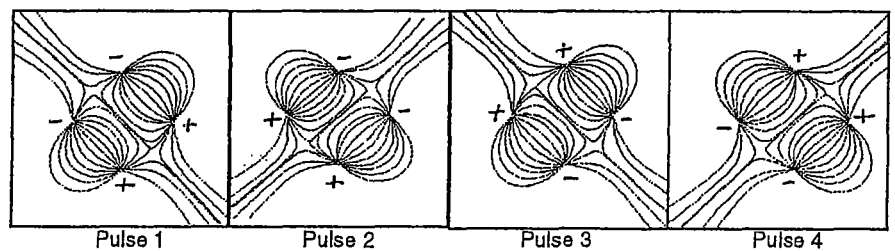

FIGURE 13B ELECTRIC FIELD LINES FOR SEQUENCE OF TABLE 12B NO REVERSING POLARITY

Three Channel Pulse Generator

| Phase | Polarity Terminal 1 | Polarity Terminal 2 | Polarity Terminal 3 |
|---|---|---|---|
| Phase 1 | Positive | Negative | Negative |
| Phase 2 | Negative | Positive | Negative |
| Phase 3 | Negative | Negative | Positive |

FIG. 15

SYSTEM FOR DISSOCIATION AND REMOVAL OF PROTEINACEOUS TISSUE

RELATED APPLICATIONS

This Application claims priority to Provisional Patent Application No. 60/755,839 filed Jan. 3, 2006.

BACKGROUND OF THE INVENTION

The present invention pertains to the dissociation and removal of highly hydrated macroscopic volumes of proteinaceous tissue; more particularly, the present invention pertains to the dissociation and removal of highly hydrated macroscopic volumes of proteinaceous tissue using rapid variable direction energy field flow fractionization.

The present invention is described in terms of vitreoretinal surgery; however, those of ordinary skill in the art will understand the applicability of this invention to medical procedures in other areas in the body of humans or animals.

For decades, prior art procedures for vitreoretinal posterior surgery have relied on mechanical or traction methods for: 1) tissue removal with shear cutting probes (utilizing either a reciprocating or rotary cutter); 2) membrane transection using scissors, a blade, or vitreous cutters; 3) membrane peeling with forceps and picks; and 4) membrane separation with forceps and viscous fluids. While improvements in mechanisms, materials, quality, manufacturability, system support, and efficacy have progressed, significant advancements in posterior intraocular surgical outcomes are primarily attributable to the knowledge, fortitude, skill, and dexterity of the operating ophthalmic physicians.

Traction-free removal of intraocular tissue during vitreoretinal surgery is nearly impossible with the current arsenal of mechanical medical instruments. Through the application of skill, precise movement, experience, and knowledge, operating physicians have been able to minimize the traction from the use of mechanical medical instruments during tissue removal but are unable to eliminate it. Mechanical or traction surgical methods utilize a shearing action to sever tissue bonds. This shearing action inherently puts tension on the tissue to be removed, that tension, in turn, is transferred to the retinal membrane. Because of the use of mechanical or traction surgical methods, the forces which impart motion to the cutting element of the mechanical medical devices being used to sever tissue bonds are superimposed on the retinal membrane. Despite the skill and the care of the ophthalmic surgeon, this superimposition of the forces associated with traction surgical methods onto the retinal membrane gives rise to the possibility of damage to the retinal membrane.

A potential traction-free surgical method that has been used in generating conformational changes in protein components involves the application of high intensity pulsed electrical fields; however, the use of a high-intensity pulsed electrical field has not made its way into delicate surgical procedures such as vitreoretinal surgery.

High-intensity pulsed electric fields have found numerous applications in the medical field, the food industry, and in the machining of micromechanical devices. Examples of medical field use include delivery of chemotherapeutic drugs into tumor cells, gene therapy, transdermal drug delivery, and bacterial decontamination of water and liquid foods. In the food industry, high-intensity ultrashort-pulsed electric fields have found commercial use in sterilization and decontamination. Finally, the machining and surface modification techniques used for Micro Electric Mechanical Systems (MEMS) chips employ high-intensity ultrashort-pulsed electrical fields.

Manipulation of biological structures, such as macromolecules, cellular membranes, intracellular organelles, and extracellular entities, has been the focus of recent research by both biophysics and biochemical engineering groups. Under the general heading of electrokinetics, the response of biological tissues to electric fields has been used in research, diagnostic, and therapeutic applications.

Non-Surgical Electrokinetic Research and Development

Basic understanding of the invention described herein is best obtained through an appreciation of some of the prior-art nonsurgical technologies now in use for biochemical molecular research, therapeutic pharmaceutical developments, sterilization techniques, commercial polymerization, plasma research, and MEMS (lab-on-a-chip) advancements. Key aspects of these prior-art technologies are described below to demonstrate other systems in which proteinaceous material has been manipulated and compromised by the delivery of high-intensity pulsed electrical fields.

Electrorheology

Electrorheology (ER) is a phenomenon in which the rheology of fluids, to include biological fluids, is modified by the imposition of electrical fields (usually low DC fields). The electrical field imposed on the fluid induces a bulk-phase transition in the fluid with the strength of the electrical field being the most important parameter, and the frequency of the electrical field generally being the least important parameter. Most colloidal ER fluids demonstrate an increase in viscoelastic effects with increased field amplitude. Interestingly, a decrease in viscoelasticity of the fluid appears at the highest field strengths, but definitive research into the effect of field strength on viscoelasticity of the fluid is lacking, and the mechanism of ER remains unknown.

Electrophoresis

Electrophoresis (or dielectrophoresis) involves the movement of particles in an electrical field toward one or another electric pole, anode, or cathode. The electrophoresis process is used to separate and purify biomolecules (e.g., DNA and RNA separation). For materials that are on the order of nanometers to micrometers, the electrophoresis process works well for both highly specific isolation of materials and determination of material properties. During electrophoresis, electrical field induced phase transition in a confined suspension is the subject of a spatially uniform AC electrical field. This electrical-field-induced phase transition follows the well-known field-induced formation of a columnar structure in a suspension. When subjected to an external electrical field, the particles within the electrical field align themselves along the field direction, forming chains and columns. The chains and columns of particles are then stretched by the actions of the electrical field and fluid flow. The time for separation and isolation of particles is on the order of minutes to hours and often involves the application of multiple secondary processes. An ionic surfactant (e.g., sodium dodecyl sulfate SDS) and sample dilution are often used to enhance macromolecular separation. Ionic surfactants have the ability to form a chemical bridge between hydrophobic and hydrophilic environments, thus disrupting or diminishing the hydrophobic connecting forces needed to maintain native protein structure.

Field Flow Fractionation

Field Flow Fractionation (FFF) is a laboratory solution separation method comparable in many ways to liquid chromatography. In general, both the materials and size range of materials separated in FFF systems are complimentary to those analyzed using electrophoresis and liquid chromatography. In FFF systems, the separation protagonist (electrical field) is applied in a direction perpendicular to the direction of separation and creates spatial and temporal separation of the sample components at the output of the FFF channel. Separation in an FFF channel is based on differences in the retention (time) of the sample components. In turn, the retention in FFF systems is a function of the differences in the physiochemical properties of the sample, the strength and mode of the applied assault, and the fluid velocity profile in the separation channel. Utilization of FFF has reduced electrophoresis times from hours to minutes.

Electric Field Flow Fractionation

Arising from the work being done in machining Micro Electric Mechanical Systems (MEMS) is Electric Field Flow Fractionation (EFFF). EFFF is a process for the ex-vivo separation of nanoparticles, proteins, and macromolecules entrained in microchannels by applying electrical fields either in the axial or in the lateral direction. This technique is currently under study in connection with MEMS microphoresis devices. The method is based on axial flow of analyte under the action of an electrical potential (unidirectional lateral electrical field). The separation performance and the retention time of particulate samples in the flow channel depend on the interaction of the sample with the electrical field applied transverse to the flow field in the channel. Dissociation of protein complexes, disruption of protein connections, and subsequent fractionization has been achieved with EFFF. An increase in retention, resulting in much better separation, has also been seen with the application of periodic (oscillating) electrical fields in EFFF.

In addition, the application of pulsed potentials with alternating polarity has been shown to increase the effectiveness of the electrical field. It has been postulated that shear plays a significant role in chain scission, since local deformation of proteinaceous tissue in any electrical field gradient is pure elongation. Quantified by a strain rate and axes of extension and compression, careful manipulation of array geometry and flow-field strength can result in significant extension of the majority of the macromolecules. Microchips have been designed that can generate rotational, extensional, and shear electrical field patterns, as long as the input voltages are changed. Separation time on a 1.25 cm chip has been reduced to approximately 5 seconds.

Electroporation

Electroporation is another nonsurgical prior-art technology that has been used to reversibly and transiently increase the permeabilization of a cell membrane. Introduced in about 1994, electroporation (EP) to enhance the delivery of drugs and genes across cell membranes in-vitro has become a standard procedure in molecular biology laboratories in the last decade. Electroporation is a technique in which pulses of electrical energy, measured in kilovolts per centimeter, having a duration in the microsecond-to-millisecond range, cause a temporary loss of the semi-permeability of cell membranes. This temporary loss of the semi-permeability of cell membranes leads to ion leakage, escape of metabolites, and increased cellular uptake of drugs, molecular probes, and DNA. Some prior-art applications of electroporation include introduction of plasmids or foreign DNA into living cells for transfection, fusion of cells to prepare hybridomas, and insertion of proteins into cell membranes. Classically, pulse durations in the order of 0.1 to 10 milliseconds and electrical field strength of kV/cm, depending on cell type and suspension media, have been utilized. The mechanism of electroporation (i.e., the opening and closing of cellular channels) is not completely understood.

Adaptations of the electroporation technology have been used for drug delivery. U.S. Pat. No. 5,869,326 and Published U.S. Patent Application 2004/0176716 both describe instruments for transcutaneous drug delivery. Published U.S. Patent Application 2004/021966 describes a catheter instrument for intravascular delivery of therapeutic drugs and in-vitro drug delivery using electrode array arrangements. U.S. Pat. No. 6,653,114 teaches a means for electrode switching. U.S. Pat. No. 6,773,736 and U.S. Pat. No. 6,746,613 have adapted electroporation technology to decontaminate products and fluids by causing cell deactivation and death. U.S. Pat. No. 6,795,728 uses electroporation-induced cell death as the basis for an apparatus and method for reducing subcutaneous fat deposits in-vivo.

Nanosecond Pulsed Electrical Field

Nanosecond Pulsed Electrical Field (nsPEF) technology is an extension of electroporation technology described above, to include in-vivo application, where a square or trapezoidal pulse formed with significantly shorter duration (1-300 ns), together with considerably higher electric fields (up to 300 kV/cm), is utilized. nsPEF evolved from advances in pulse-power technology. The use of this pulse-power technology has lead to the application of nanosecond-pulsed electronic fields (nsPEF) with field intensities several hundred times higher than the pulses of electrical energy used in electroporation to cells and tissues without causing biologically significant temperature increases in the samples tested. Using very few pulses of electrical energy, the effects of nsPEF are essentially non-thermal. In contrast to classical electroporation techniques, the effects of nsPEF on mammalian cells have only recently been explored. Application of nsPEF of appropriate amplitude and duration creates transient cellular permeability increases, cellular or subcellular damage, or even apoptosis. In in-vivo nanosecond electroporation, the goal is to obtain an even distribution of an efficacious electrical field within a narrow time window.

Current research has shown that the application of nanosecond pulses (kV/cm) to tissues can energize electrons without heating ions or neutral particles. It has been found that an ultrashort-pulsed energy field (Electromagnetic EM, Laser, or High Intensity Focused Ultrasound HIFU) can be used to temporarily and reversibly increase the permeability of cell membranes or even compromise intracellular components without affecting the cell membrane. It has also been found that higher energies will excite ions and may cause the formation of short-lived radicals (OH and $O_2^+$). This finding has lead to the development of processes for sterilization and decontamination whereby cells are killed. The use of still higher energies may cause the formation of super-charged plasma arcs which attack cellular bonds at the molecular level.

Electro-Osmosis

Electro-osmosis (EO) is a technique used to transport or mix fluid for use in micro devices. A key concept is to exploit different charging mechanisms and polarization strength of the double layer at the electrode/electrolyte interface, to produce a unidirectional Maxwell force on the fluid, which force generates through-flow pumping. In "induced-charge electro-osmosis" (ICEO), an effect is created which produces micro-vortices within a fluid to enhance mixing in microfluidic devices. Mixing can be greatly enhanced in the laminar flow regime by subjecting the fluid to chaotic-flow kinematics. By changing the polarity and the applied voltage, the strength and direction of the radial electro-osmotic flow can be controlled.

Other Electrokinetic Phenomena

Electrokinetic phenomena are not limited to that described above. Recent variants associated with very large voltages and unique electrical fields in MEMS research have demonstrated interesting and counter-intuitive effects occurring with variable applied electrical fields, including the finding that the electrophoretic mobility of colloids is sensitive to the distribution of charges, rather than simply the total net charge.

Tissue Removal

All of the processes described above are applicable to manipulation of macromolecules, but not to the extraction or removal of macroscopic volumes of proteinaceous tissue by tissue dissociation. As other systems using pulsed energy with tissues employ high levels of energy, it has been found that higher energies delivered through the use of longer pulse durations, pulse trains, repetition rates, and exposure times will cause thermal effects or the formation of super-charged plasma. These thermal effects or the formation of super-charged plasma have been effectively utilized in several devices to develop surgical instruments for tissue cutting. In these instruments, a microsize (thickness or projection) plasma region is created about an instrument. Within the super-charged plasma are charged electrons, ions, and molecules with an erratic motion which, when contacted with tissues or cells, attack bonds at the molecular level—thereby ablating or obliterating via sublimation the target tissue or tissue surface. The formation of super-charged plasma relies on electron avalanche processes—high rate of tunneling by electrons from the valence band to the continuum to form electron plasma avalanche ionization. The density of this super-charged plasma rapidly builds up by virtue of additional tunneling as well as field-driven collisions between free electrons and molecules. A major goal of the treatment of tissue with super-charged plasma is nondestructive surgery; that is, controlled, high-precision removal of diseased sections with minimum damage to nondiseased tissue. The size and shape of the active plasma are controlled by probe design, dimensions, and media. Both gaseous and fluid media have been employed. Within a liquid, an explosive vapor may be formed.

Pulsed Electron Avalanche Knife

The Pulsed Electron Avalanche Knife (PEAK) disclosed in Published U.S. Patent Application 2004/0236321 is described as a tractionless cold-cutting device. A high electrical field (nsPEF 1 to 8 kV, 150 to 670 uJ) is applied between an exposed microelectrode and a partially insulated electrode. The application of this high electrical field leads to a plasma formation manifested in the form of micrometer-length plasma streamers. It is the size of the exposed electrode which controls the dimensions of the plasma streamers. The plasma streamers, in turn, create an explosive evaporation of water on a micron scale. Pulsed energy is critical. Precise, safe, and cost-effective tissue cutting has been demonstrated. Even with the electrode scaled down in size to the micron level, the plasma discharges must be confined to the probe tip, because ionization and explosive evaporation of liquid medium can disrupt the adjacent tissue and result in cavitation bubble formation. The high pressure achieved during plasma formation, the fast expansion of vapor bubble (>100 m/sec), and the subsequent collapse of the cavity that can extend the zone of interaction is mainly mechanical due to rapid bubble vapor cool down. In ophthalmic surgery, the volatility and aggressiveness of the effect caused by the use of a PEAK could be detrimental to retinal integrity.

Coblation

Coblation, or "Cold Ablation," uses radio frequency RF in a bipolar mode with a conductive solution, such as saline, to generate plasma which, when brought into contact with a target tissue, sublimates the surface layer of the target tissue. The range of accelerated charged particles is short and is confined to the plasma boundary layer about the probe and to the surface of tissue contact. Coblation energizes the ions in a saline-conductive solution to form a small plasma field. The plasma has enough energy to break the tissue's molecular bonds, creating an ablative path. The thermal effect of this process has been reported to be approximately 45-85° C. Classically, RF electrosurgical devices use heat to modify tissue structure. The generation of a radio frequency induced plasma field, however, is viewed as a "cold" process, since the influence of the plasma is constrained to the plasma proper, and the plasma layer maintained is microscopically thin. The plasma is comprised of highly ionized particles of sufficient energy to achieve molecular dissociation of the molecular bonds. The energy needed to break the carbon-carbon and carbon-nitrogen bonds is on the order of 3-4 eV. It is estimated that the Coblation technique supplies about 8 eV. Due to the bipolar configuration of the electrodes and the impedance differential between the tissue and the saline solution, most of the current passes through the conductive medium located between the electrodes, resulting in minimal current penetration into the tissue and minimal thermal injury to the tissue. If the threshold of energy required to create plasma is not reached, current flows through the conductive medium and the tissue. Energy absorbed by both the tissue and the conductive medium are dissipated as heat. When the threshold of energy needed to create plasma is reached, impedance to RF current flow changes from almost purely resistive-type impedance into a more capacitive-type impedance. Similar to the drawbacks of the PEAK for ophthalmic surgery, the use of coblation techniques may be too aggressive for surgical applications near the retina.

Plasma Needle

The plasma needle is yet another device that allows specific cell removal or rearrangement without influencing surrounding tissue. Use of the plasma needle is a very exacting technique which utilizes a microsize needle affixed to a hand-operated tool to create a small plasma discharge. An electrical field is created between the needle tip and a proximal electrode with an inert gas (helium) flowing there between. The small plasma discharge contains electrons, ions, and radicals—with the ions and radicals controllable by the introduction of a contaminant, such as air, into the inert gas. It has been postulated that the small size of the plasma source (plasma needle) creates ROS (reactive oxygen species) and UV light emissions at such minute levels as to alter cell function or cell adhesion without damaging the cells themselves. However, an increase in ROS (i.e., air) in the inert gas along with an increased irradiation time can lead to cell death. While shown to exert an influence across thin liquid layers, use of the plasma needle is not optimal in a total liquid environment, as often found in ophthalmic surgery.

Spark Erosion

Spark erosion technology is a cousin to the plasma technologies discussed above. The spark erosion device utilizes a pulsed energy field of 250 kHz, 10 ms duration, and up to 1.2 kV to produce a vapor. As the electric breakdown of vapor occurs, a small spark (<1 mm) is formed. With up to a 1.7 mm far-field effect, the cutting performance from spark erosion is similar to electrosurgery, but, like plasma—only the plasma contacts tissue.

Lasers

Lasers represent another traction-free technology that has been used to break down tissue macro molecules. Lasers have been utilized in ophthalmic surgery since about 1960. The greatest success in laser usage has been in the area of non-invasive retinal coagulation in diseases such as diabetic retinopathy, central vein occlusion, and choroidal neovascularization in age-related macular degeneration or ischemic retinal vasculitis. Lasers have also been used extensively in anterior eye applications for such applications as corneal sculpting and glaucoma. Attempts to utilize lasers in posterior ophthalmic surgeries have achieved mixed results. Non-invasive (trans-corneal/lens or trans-sclera) techniques are not practical, due to the absorptive properties of these intervening tissues. The extraordinary precision needed in intraocular surgery of the retina and vitreous requires the use of increasingly refined invasive techniques for tissue manipulation and removal. The tissue/laser interaction regimes include 1) thermal—conversion of electromagnetic energy into thermal energy; 2) photochemical—intrinsic (endogenous) or injected (exogenous) photosensitive chemicals (chromophores), activated by absorption of laser photos; 3) photoablative—direct photodissociation of intramolecular bonds of absorption of photons; and 4) electromechanical—thermionic emission or multiphoton production of free electrons leading to dielectric breakdown and plasma production. It has been found that lasers are costly and require the use of shields and backstops on uniquely designed laser probes to protect fine intraocular tissues from stray laser energy and far-field thermal effects. However, recent developments in femtosecond-pulsed lasers have opened new possibilities in fine surgical applications.

Other Tissue Removal Methods

Methods currently employed to disrupt intraocular tissues include morcellation (fragmentation), which is the objective of mechanically shearing vitrectomy devices; liquefaction as accomplished by thermal (protein denaturizing) or enzymatic reactions; and sublimation via laser or plasma treatments. Sublimation via laser or plasma treatments actually compromises bonds on a molecular level, whereas morcellation and liquefaction affect the binding mechanism of lesser strength (i.e., non-covalent bonds).

Accordingly, despite many advances in vitreoretinal surgery, a need still remains for an effective apparatus and method for the dissociation and removal of highly hydrated macroscopic volumes of protein tissues, such as vitreous and intraocular tissues, during vitreoretinal surgery.

SUMMARY

The present invention describes an apparatus and method for the dissociation and removal of highly hydrated macroscopic volumes of proteinaceous tissues, such as vitreous and intraocular tissue, during vitreoretinal surgery.

While the disclosed invention is described in terms of an instrument and method for traction-free removal of vitreous and intraocular membranes from the posterior region of the eye without damaging the ultrafine structure and function of the adjacent or adherent retina, those of ordinary skill in the art will understand the applicability of the disclosed invention for other medical procedures on both humans and animals.

The disclosed invention is described in terms of a new means of performing vitreoretinal surgery using a high-intensity short directionally changing electrical field, as opposed to classical mechanical means to engage, decompose, and remove vitreous and intraocular tissues. Specifically, the following disclosure affects the discovery that a transient change in tissue condition caused by the application of a high-intensity short directionally changing electrical field is satisfactory for removal of macroscopic volumes of proteinaceous tissue. The technical success of mechanical and liquefying means supports the contention that vitreous material need not be obliterated or disrupted on a molecular level to be removed—but, rather, an innocuous macroscopic change of state is all that is needed for tissue removal. Accordingly, the removal of intraocular tissue enabled by the disclosed invention is entirely traction-free.

The apparatus and method disclosed herein causes a local temporary dissociation of the adhesive and structural relations in components of intraocular proteinaceous tissue using a rapidly changing electrical field. This localized temporary dissociation of the adhesive and structural relations between components of intraocular proteinaceous tissue enables tractionless detachment between intraocular tissue components and the retinal membrane. Fluidic techniques (irrigation and aspiration) are utilized during the tissue dissociation process to enhance the formation of a high-intensity ultrashort-pulsed electrical field and to remove disrupted tissue at the moment of dissociation. It is intended that only the material within the applied high-intensity ultrashort-pulsed electrical field is assaulted and removed. Therefore, because only the material assaulted by the applied ultrashort pulses receives the high-intensity ultrashort-pulsed electrical field, there is no far-field effect during the tissue extraction process.

The design of the probe used to create the pulsed electrical field coupled with the use of fluidic techniques entrains the target macroscopic volume of tissue to be dissociated. Simultaneously, therefore, the entrained target macroscopic volume of intraocular tissue is subjected to a high-intensity ultrashort-pulsed electric field assault. This high-intensity ultrashort-pulsed electrical field assault leads to dissociation of the entrained macroscopic volume of intraocular proteinaceous tissue, and then aspiration removes the dissociated entrained macroscopic volume of tissue.

According to the disclosed invention, a probe with two or more electrodes is inserted into the target hydrated tissue, vitreous or intraocular tissue. The ends of the electrodes are exposed at the distal end of the probe. An electrical pulse is transmitted down at least one of the electrodes while the other one or more electrodes act as the return conductors. A non-plasma electrical field is created between the delivery electrode(s) acting as an anode and the return electrode(s) acting as a cathode. With each electric pulse, the direction of the created electrical field is changed by reversing polarity, by electrode switching or by a combination of both. Pulses may be grouped into burst reoccurring at different frequencies and different amplitudes. Such pulse groups may be directed at heterogeneous tissue. The electrical pulse amplitude, duration, duty cycle and repetition rate along with continual changing of field direction, create the disruptive electrical field created across the orifice of the aspiration lumen. Tissue is drawn into the orifice of the aspiration lumen by fluidic techniques (aspiration). The tissue is then mixed or diluted with irrigation fluid and disassociated as it traverses the high-intensity ultrashort-pulsed directionally changing electric field. At any given instant, disorder is created in the electrical field by changing the direction of the electrical field between one or more of the electrodes at the tip of the probe. The affected medium between the electrode terminations at the end of the probe consists of a mix of target tissue (e.g. vitreous) and supplemental fluid (irrigation fluid). The electrical impedance of this target medium in which the electrical field is created is maintained by the controlled delivery of supplemental fluid (irrigation fluid). In the preferred embodiment, the supplemental fluid providing the electrical impedance is a conductive saline. The supplemental fluid may be provided by an irrigation source external to the probe, through one or more lumens within the probe or a combination of both. When the supplemental fluid is provided within an constrained to the probe interior, the supplemental fluid may have properties (e.g. pH) and ingredients (e.g. surfactants) that may be conducive to protein dissociation.

Critical to the operation of the disclosed invention are the properties of the generated electrical energy field within the target medium. Herein, high-intensity, ultrashort pulses (sub-microseconds) of electrical energy are used. Tissue impedance, conductivity and dilution are maintained in the target medium by supplemental fluid irrigation. The pulse shape, the pulse repetition rate, and the pulse train length are tuned to the properties of the intraocular tissues. Multiple pulse patterns may be employed to address the heterogeneity of intraocular tissue. In addition, the spatial termination and the activation sequence of the electrodes at the tip of the probe, along with the generated field profile, play a significant role in tissue decomposition. The fluid aspiration rate is matched to the tissue dissociation rate. The pulsed rapid disruptive electric field effect in the target medium is of such high intensity, but such short duration (i.e., low energy), that the actual dissociation of the targeted tissue from surrounding tissue is a transient effect (microseconds to milliseconds), which is non-thermal, and devoid of explosive cavitation.

The energies delivered by the ultrashort duration, high-intensity electrical pulses do not cause plasma formation; thus, there is no aggressive far-field effect. The ultrashort duration, high-intensity electrical pulses are used to create a non-contact disruptive electrical force within the tissue, not by an electron avalanche but, rather, by a continual change in field direction. Specifically, a non-plasma, non-contact energized region of disorder is created in the proteinaceous tissue to be dissociated. Any charged material entering into the electric field will be affected by that field, and intraocular tissues (e.g., proteins) will be changed. By creating a disruptive electric field about proteinaceous tissues without creating an electron avalanche, the attachment mechanisms between the tissue components experience a transient compromise. This transient compromise leads to a dissociation of tissue components—free of far-field perturbations. This transient compromise of tissue attachment mechanisms between the tissue complexes leads to the unfolding of protein complexes and the uncoiling of helices, thereby allowing for disruption of collagen segments and adhesive bonds (fragmentation of staggered fibrils).

The intended purpose of the work leading to the discovery of the disclosed invention described herein has been the tractionless extraction of vitreous and intraocular membranous tissues from the posterior intraocular region of the eye. The disclosed apparatus and method engage and disrupt a hydrated proteinaceous gel matrix causing a transient compromise or dissociation of the adhesive mechanisms between tissue components. During this transient compromise or dissociation of the adhesive mechanisms between tissue components, fluidic techniques are employed to dilute and aspirate the dissociated tissue complex from the surrounding tissue.

The purpose of the system disclosed herein is also to alter the state of vitreous proteinaceous tissue for safe removal. This alteration of the state of vitreous proteinaceous tissue entails the disruption of proteinaceous tissue component interactions, the promotion of separation and detachment of proteinaceous tissue components from adjacent structures, and, while proteinaceous tissue components are separated and detached—their removal.

Accordingly, it is an object of this disclosure to present a new surgical device modality and device that addresses the needs of the modern vitreoretinal surgeon—namely, a device for improved and more precise extraction of vitreous and intraocular membranes while preserving retinal integrity. Though this disclosed system is focused on a new device for altering the state of and removal of the corpus vitreous and associated intraocular membranes, it will become obvious to one skilled in the art that the information presented herein is applicable to other surgical arenas besides ophthalmology.

BRIEF DESCRIPTION OF THE DRAWING FIGURES

A better understanding of the disclosed system for dissociation and removal of proteinaceous tissue may be had by reference to the drawing figures wherein.

Figure 6:
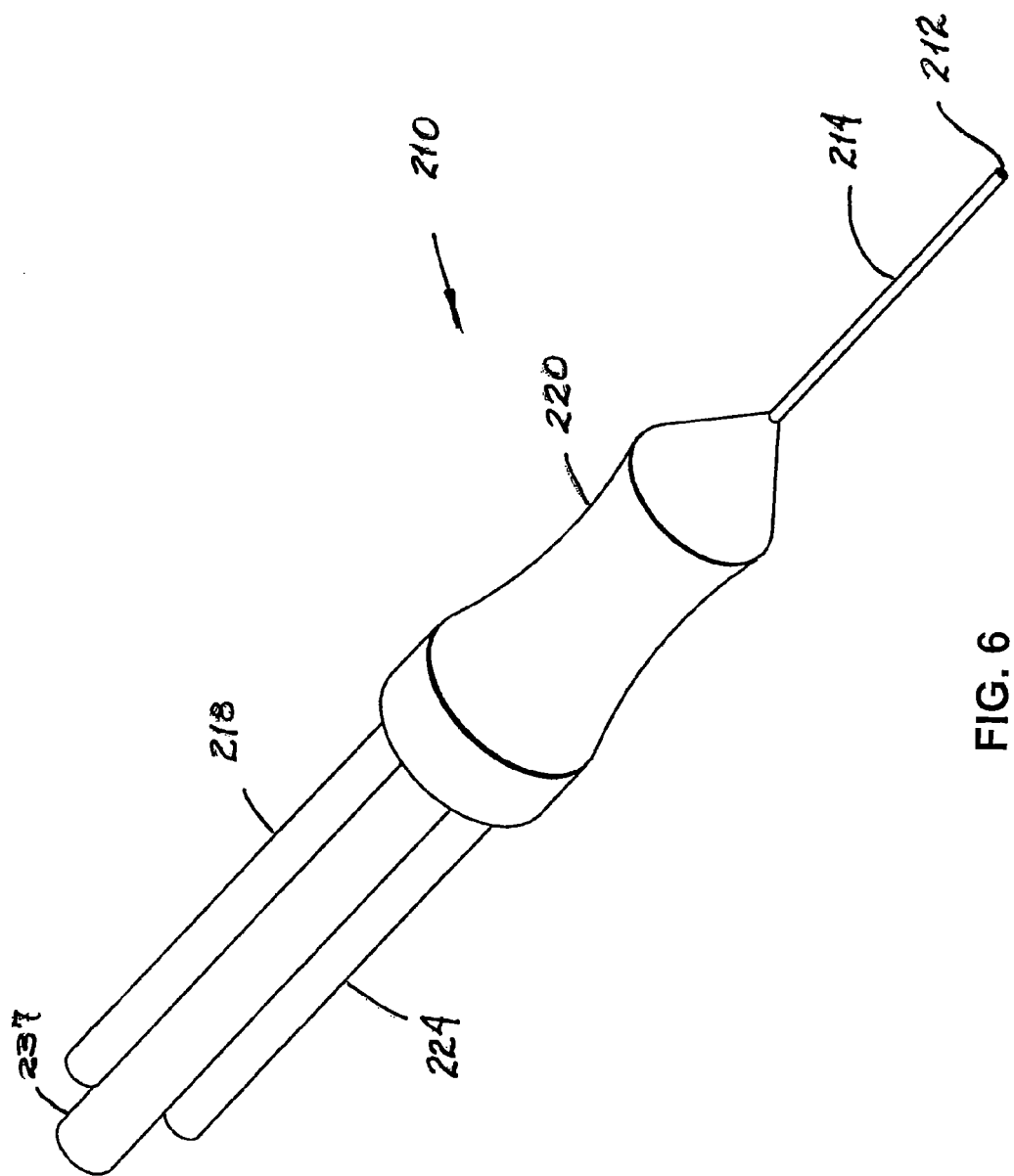
Figure 9:
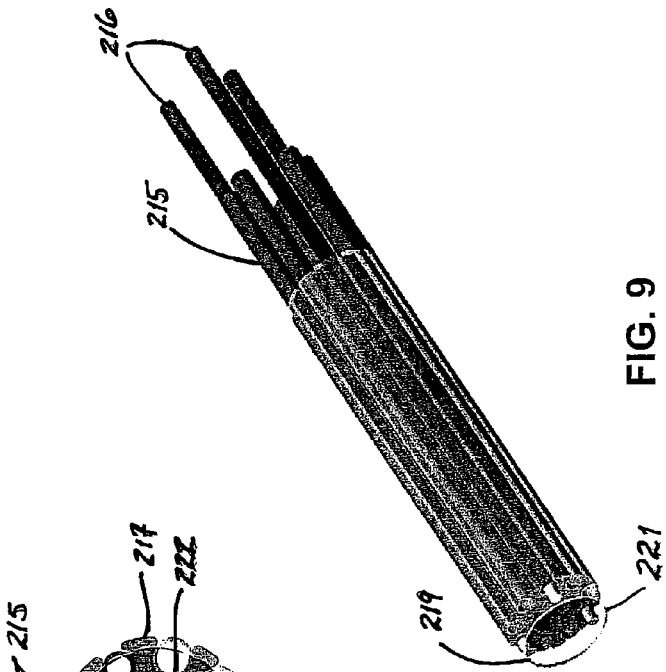
Figure 8:
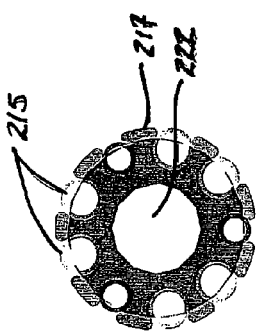
Figure 7:
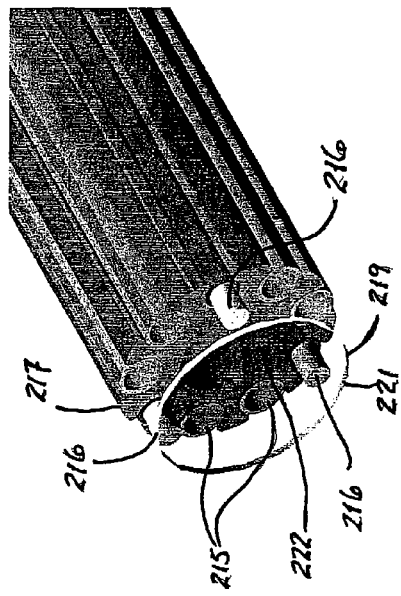
Figure 10:
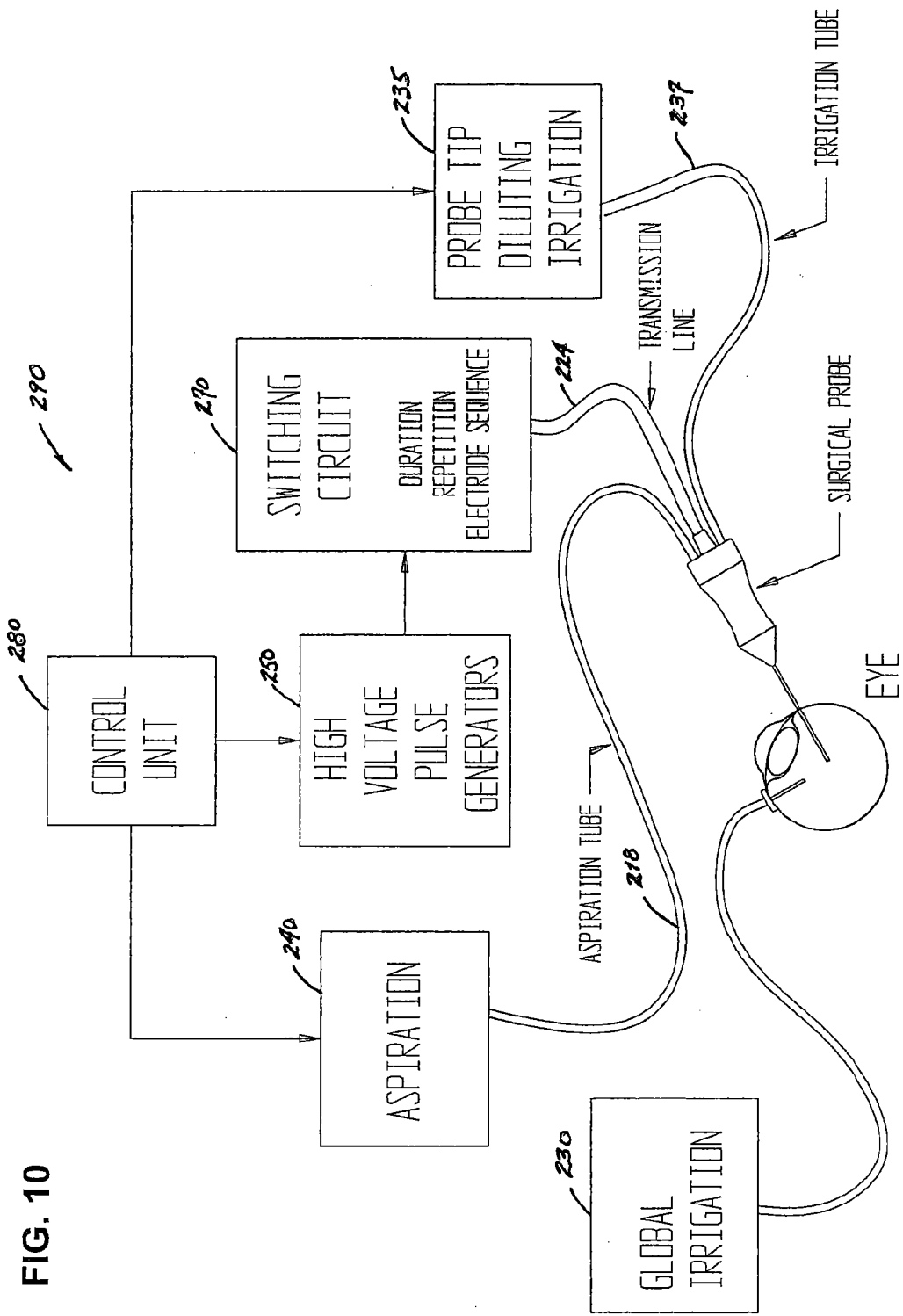
Figure 14:
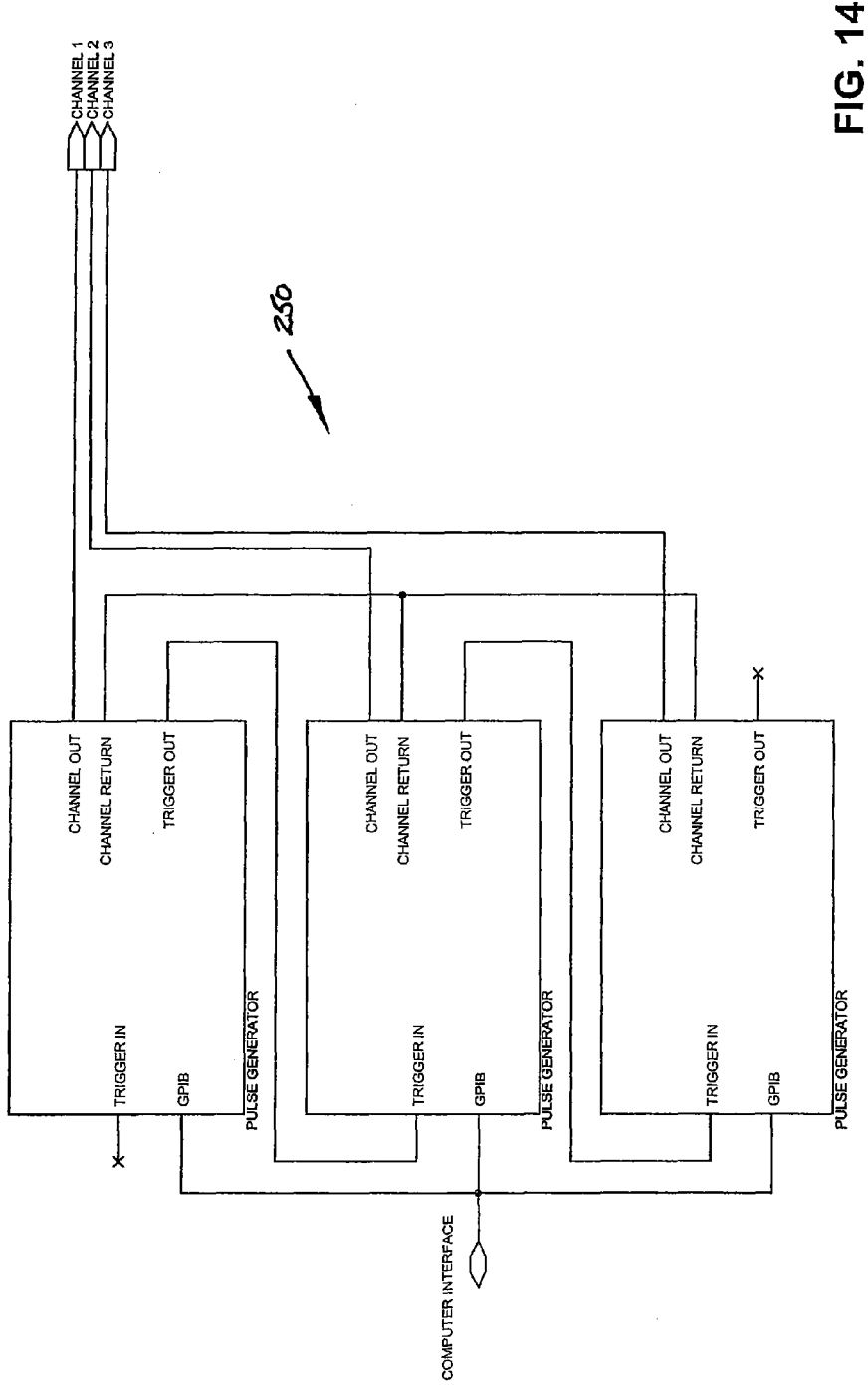
Figure 16:
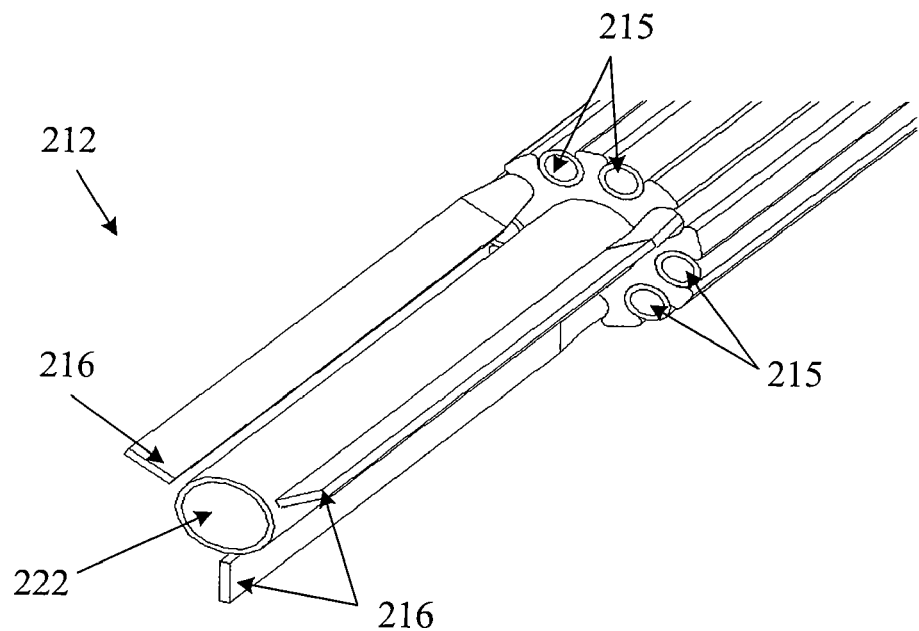
Figure 17:
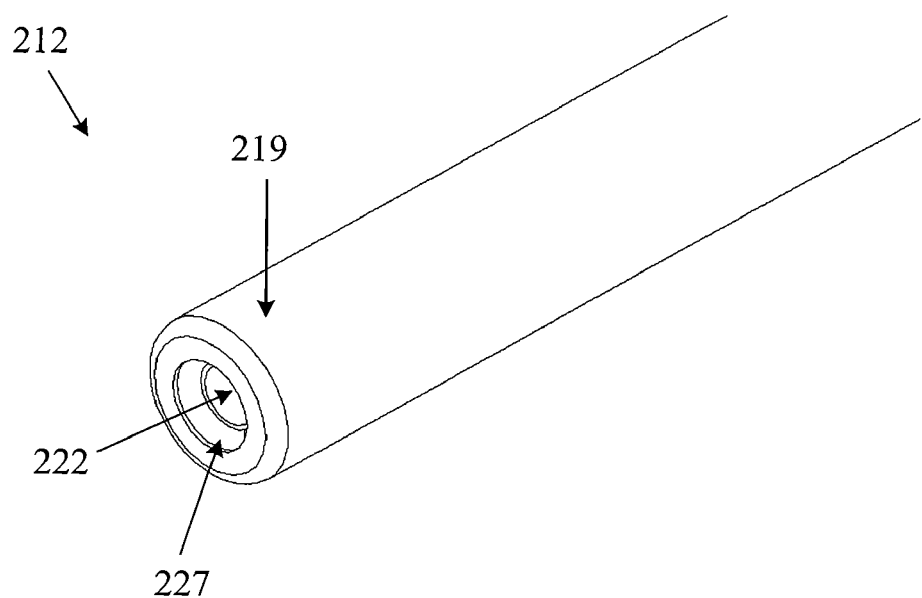
Figure 18:
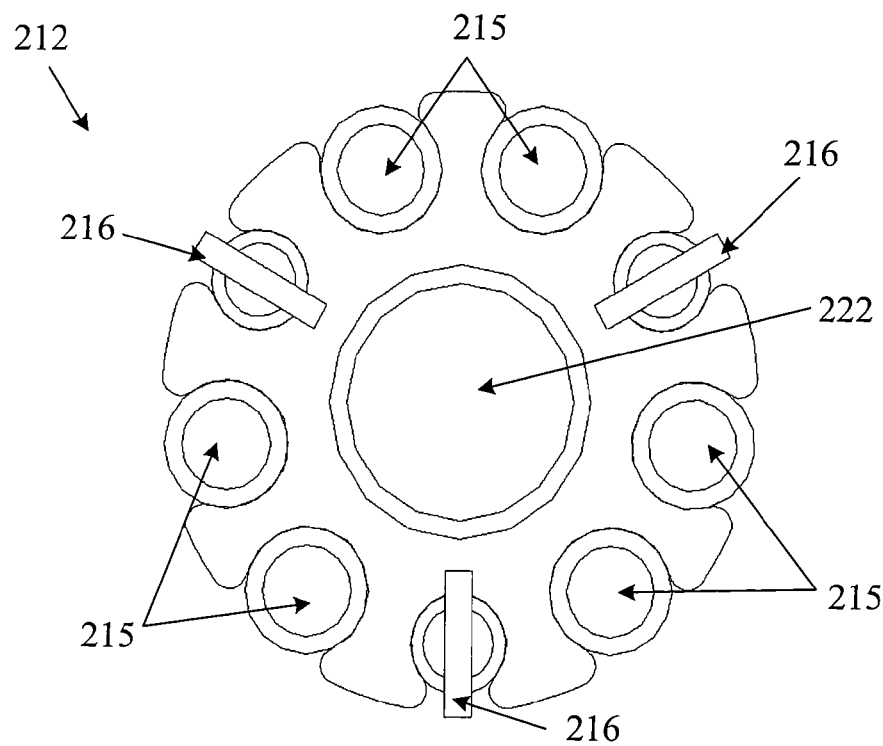
Figure 19:
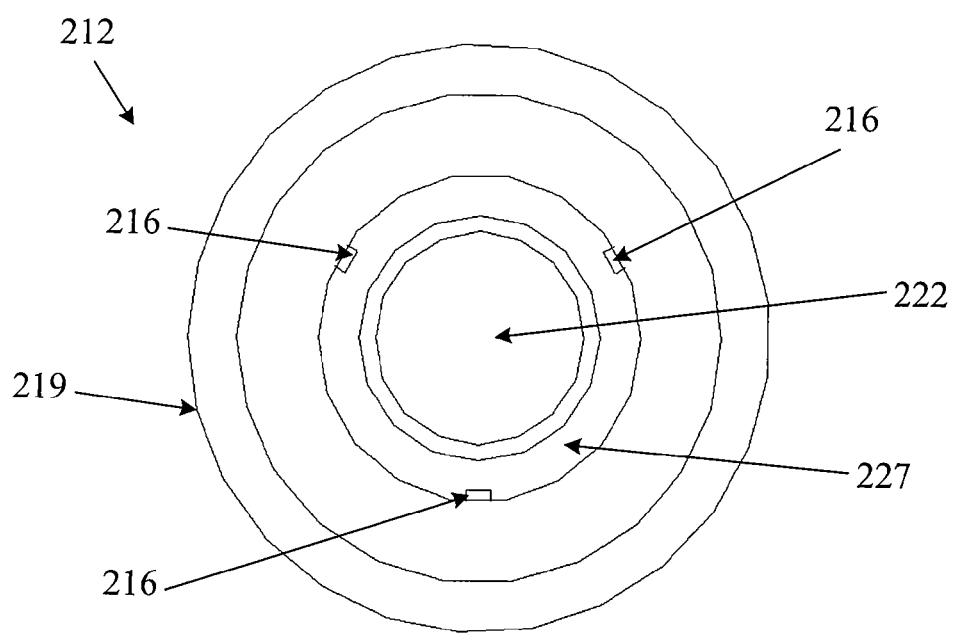
Figure 20:
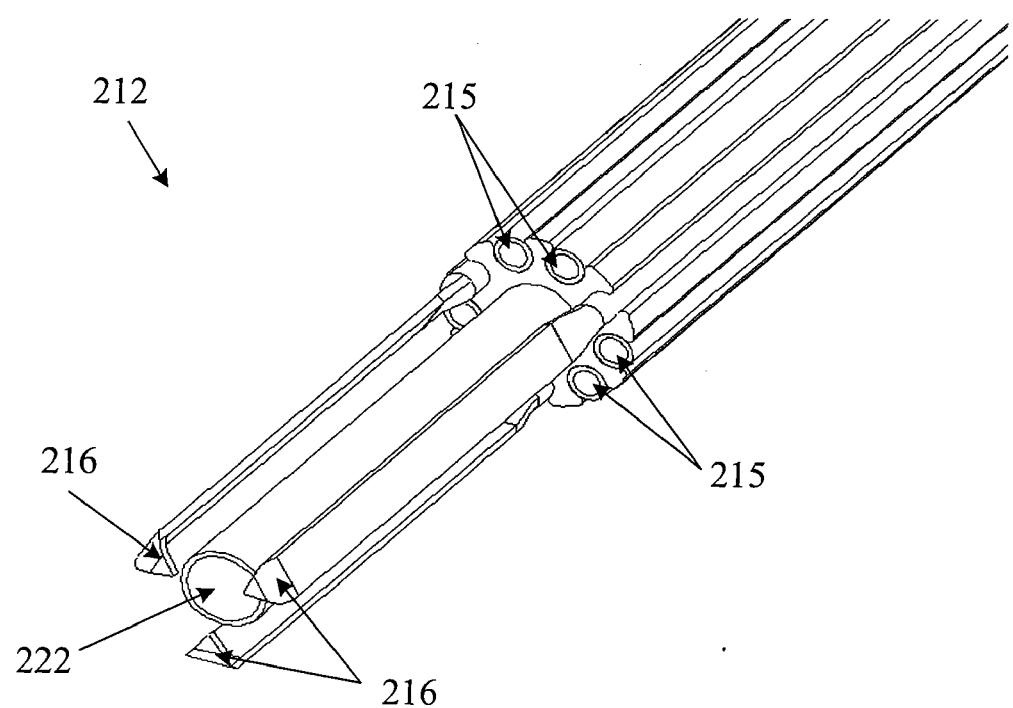
Figure 21:
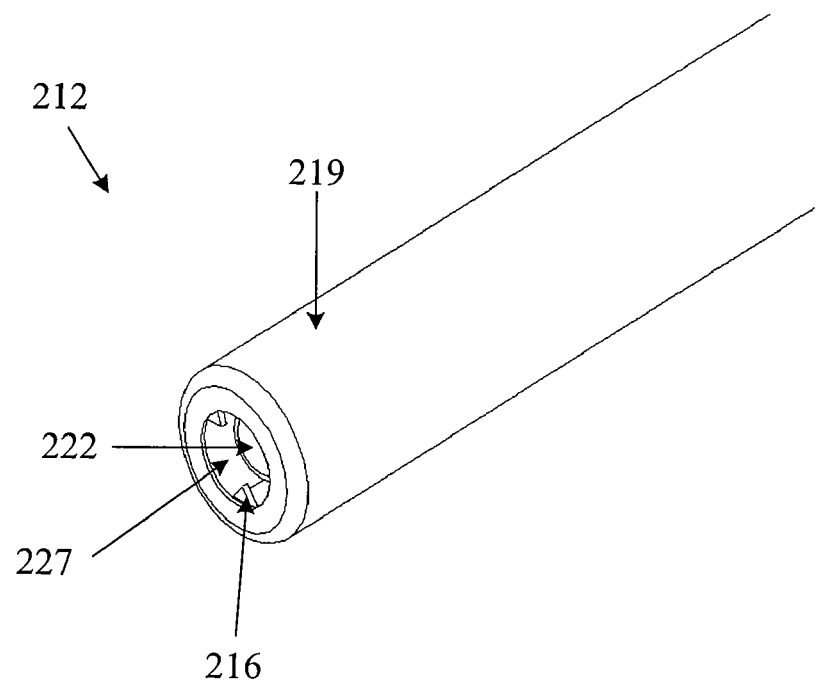
Figure 22:
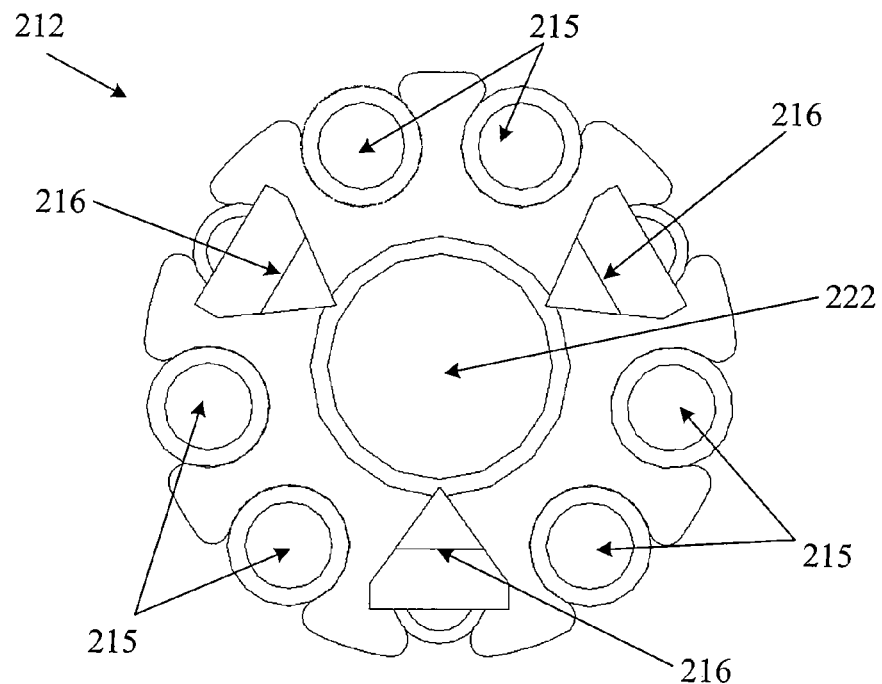
Figure 23:
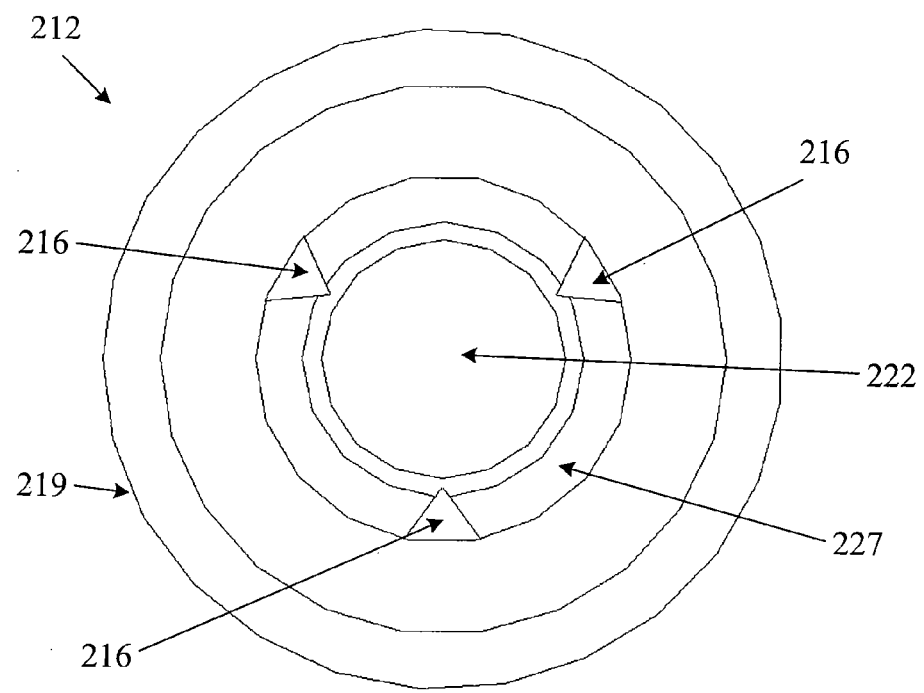

FIGS. 4A, 4B, 4C, 4D, and 4E are front views of alternative placements of electrodes on the tip of the probe;

Tables 5A, 5B, 5C, 5D, and 5E are activation schemes associated with the probe arrays shown in FIGS. 4A, 4B, 4C, 4D, and 4E, respectively;

FIG. 6 is a perspective view of three electrode embodiment of the probe used for intraocular posterior surgery employing the system of the disclosed invention;

FIG. 7 is an enlarged perspective view of the tip of the probe shown in FIG. 6 including a transparent cover to reveal the interior features;

FIG. 8 is an end view of probe shown in FIG. 7;

FIG. 9 is an expanded perspective view of the probe similar to that shown in FIG. 7;

FIG. 10 is a schematic diagram of an alternate embodiment of the disclosed system with a supplemental irrigation means included in the probe;

FIG. 11A is an end view of the probe tip showing the placement of three electrodes as in the embodiment shown in FIGS. 7, 8, and 9;

FIG. 11B is an end view of a probe tip having four electrodes;

FIG. 12A is an activation scheme associated with the electrode array shown in FIG. 11A;

FIG. 12B is an activation scheme associated with the electrode array shown in FIG. 11B;

FIG. 13A is an illustration of exemplary field lines resulting from placement of a charge on one or more of the electrodes displayed in FIG. 11A;

FIG. 13B is an illustration of exemplary field lines resulting from placement of a charge on one or more of the electrodes displayed in FIG. 11B;

FIG. 14 is a schematic diagram of an exemplary three-channel pulse generator used with a three-electrode probe;

FIG. 15 is a schematic diagram of the channel states during a single cycle of pulsing of the generators shown in FIG. 14;

FIG. 16 is an enlarged perspective view of another embodiment of the tip of the probe shown in FIG. 6 including a transparent cover to reveal the interior features;

FIG. 17 is an enlarged perspective view of the probe shown in FIG. 16 including a jacket that covers the interior features;
FIG. 18 is an end view of probe shown in FIG. 16;
FIG. 19 is an end view of probe shown in FIG. 17;
FIG. 20 is an enlarged perspective view of another embodiment of the tip of the probe shown in FIG. 6 including a transparent cover to reveal the interior features;
FIG. 21 is an enlarged perspective view of the probe shown in FIG. 20 including a jacket that covers the interior features;
FIG. 22 is an end view of probe shown in FIG. 20; and
FIG. 23 is an end view of probe shown in FIG. 21.

DETAILED DESCRIPTION OF THE EMBODIMENTS

Liquefaction (synchysis) is manifested in vitreous portion of the eye as a natural consequence of aging. As an individual reaches 70 to 90 years, roughly 50% of the vitreous gel structure has gone through a change of state or become liquefied. The results of synchysis are realized in the posterior vitreous as a destabilization of the vitreous matrix, dissolution of HA-collagen coupling, unwinding of collagen helices, molecular rearrangements, increases in the volume of liquefied spaces, loosening of entangled tethers, increases in vitreous detachment from the retina, collagen fiber fragmentation and aggregation, and loss of proteoglycans, non-covalent bound macromolecules and adhesive collagen (type IX). At the cellular level, many of the activities leading to liquefaction in the vitreous portion of the eye may be emulated by the present invention.

The apparatus and method of the disclosed invention deliver a variable direction, pulsed high-intensity and ultrashort duration disruptive electric field (low energy) at a pulse duration, repetition rate, pulse pattern, and pulse train length tuned to the properties of the components of the intraocular extracellular matrix (ECM) to create a short period of tissue dissociation. The recommended modality of ultrashort-pulsed disruptive electric field application relies on the delivery of high powers of low energy.

Figure 1:
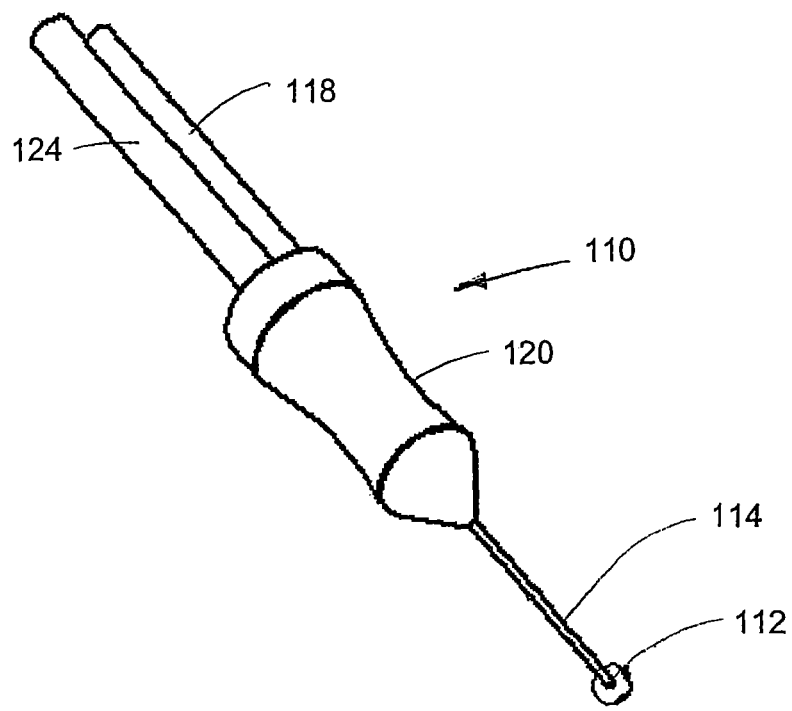
FIG. 1 is a perspective view of a probe used for intraocular posterior surgery on which the system of the disclosed invention is used.
Figure 2:
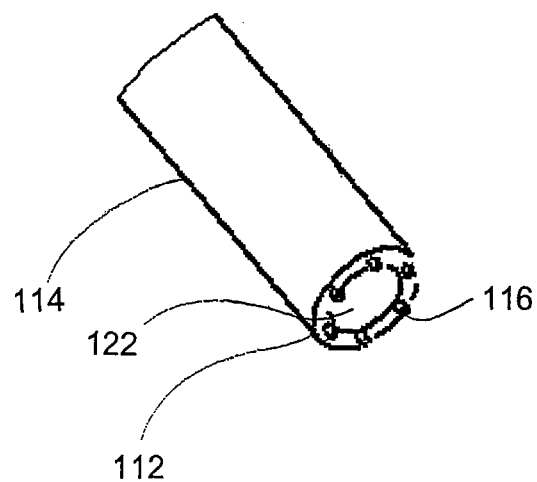
FIG. 2 is an enlarged perspective view of the tip of the probe shown in FIG. 1.

As shown in FIG. 1, the disclosed apparatus for implementing the current invention includes a probe assembly 110 which delivers, channels, and distributes the energy applied to the soft tissue in such a fashion as to create a confined, localized, non-thermal dynamic region of electrical forces within a macroscopic volume of the extracellular matrix ECM (e.g., vitreous and intraocular membranes) leading to momentary dissociation of proteinaceous complexes and local liquefaction of the entrained macroscopic volume of tissue. The tip 112 of the hollow probe 114 is positioned to encircle the entrained macroscopic volume of proteinaceous tissue. Fluidic techniques (irrigation) are used first to provide a region of stable impedance and dilution between the electrodes 116 at the tip 112 of the hollow probe 114 and then draw in and remove (aspiration) the affected macroscopic volume of proteinaceous tissue before the reassembly of non-covalent proteinaceous relationships can occur. The fluidic techniques used with the probe assembly 110 may include both saline irrigation and effluent aspiration.

The directionally changing electrical field created at the tip 112 of the hollow probe 114 is presented substantially perpendicular or orthogonal to the direction of carrier fluid movement (i.e., proteinaceous material in a water solution). The direction of the electrical field is changed with every or nearly every pulse. Pulse duration (nanoseconds) is short, relative to the dielectric relaxation time of protein complexes (~1 ms). Multiple pulse direction changes may occur within the dielectric relaxation time interval. Pulse duration, pulse repetition rate, pulse pattern, and pulse train length are chosen to avoid the development of thermal effects ("cold" process). The disclosed system generates and delivers square-shaped pulses of variable direction with fast (<5 nanoseconds) rise time and fall time. The shorter the rise and fall times of the pulse, the higher the frequency components in the Fourier spectrum of the pulse and, consequently, the smaller the structures that can be affected by the pulse. In the system for dissociation and removal of proteinaceous tissue disclosed herein, pulse durations are in the nanosecond range, and the electric field strength would be greater than 1 kV/cm, preferably in the range of hundreds (100s) of kV/cm.

The apparatus and method which effect the system of the disclosed invention utilize ultrashort chaotic high-intensity pulsed electric field flow fractionation (CHIP EFFF) to engage, dissociate, and remove vitreous and intraocular membranous material. A stepwise continual change in direction of the field (by use of an array of electrodes 116) created by reversing polarity, switching active electrodes or a combination of both is incorporated into the tip 112 of the hollow probe 114 to create a disruptive effect on charges involved in the non-covalent bonds holding the vitreous complexes (groups of proteins) together. By making the macroscopic volume of intraocular electrically unstable tissue, it is possible to further weaken the hydrophobic and hydrostatic bonds within the captured proteinaceous tissue, membranes, and multi-component enzymes, thereby increasing the fluidity or liquefaction of the tissue. The resulting assault on the hydrophobic and hydrostatic bonds of the proteinaceous tissue is sufficient for a momentary compromise of the binding mechanisms of the adhesive macromolecules of the vitreous and associated intraocular tissue, thereby temporarily reducing a minute portion of the bulk vitreous material to a manageable free proteinaceous liquid complex.

Paramount to the efficacy of the disclosed invention is the choice of energy. The object of the assault on the bonds which hold proteinaceous tissue together is to create disorder among electrons in the outer shell of the macromolecules associated with non-covalent bonds. The preferable form of energy is electricity—energizing electrons by the direct creation of an electric field. Other sources of energy, such as microwaves, and ultrasound which utilize photons and phonons to energize electrons, may also be used to create a disruptive field. It is appreciated herein that lasers, particularly those operating with pulse durations in the femtosecond range and at frequencies substantially at the peak absorption frequency of water, may also be utilized as an alternative energy source.

In the preferred embodiment of the apparatus and method disclosed herein, a rapid variable direction electric field flow fractionation is used to engage, to dissociate, and to remove vitreous and intraocular membranous material. Specifically, the disclosed system utilizes high-intensity ultrashort-pulsed disruptive electrical field characterized by continuous changes of field direction coupled with fluidic techniques both to facilitate creation of the electrical field and then to remove the proteinaceous dissociated tissue. The high-intensity ultrashort-pulsed disruptive electric field is generated using field strengths on the order of kV/cm with pulse widths on the order of nanoseconds. The high-intensity ultrashort-pulsed disruptive electrical field is kept substantially orthogonal to the direction of aspirating carrier fluid flow. A stepwise continual change in the direction of the high-intensity ultrashort-pulsed disruptive electrical field (created by reversing polarity or switching between an array of electrodes) is adopted to create disorder among the electrons involved in the non-covalent bonds holding the tissue complexes (groups of proteins) together. Using pulse durations and pulse trains that are short with respect to the time required for thermal effects, the assault on the tissue-binding mechanisms is essentially a "cold" process and sufficient for momentary tissue matrix dissociation. The assault on the tissue-binding mechanisms will compromise the binding mechanisms of the adhesive macromolecules of the vitreous and associated intraocular tissue, thereby temporarily reducing a minute portion of the bulk vitreous material to a manageable proteinaceous liquid complex. The strength of the electrical field causing the disassociation obeys the inverse square law. As such, the strength of the field is highest in region between electrodes. In the preferred embodiment, this distance is less than 0.5 millimeters. The affected proteinaceous liquid complex is localized within the region of applied pulsed rapid variable direction electrical field between probe electrodes and is removed using fluidic techniques (aspiration) before the transient effects of the assault on the tissue-binding mechanism expire (relax). Once the volume of proteinaceous tissue is in the extraction channel (i.e., within the fluidic aspiration stream), the state of the altered proteinaceous complex may return to a quasi pre-assault state.

Figure 3:
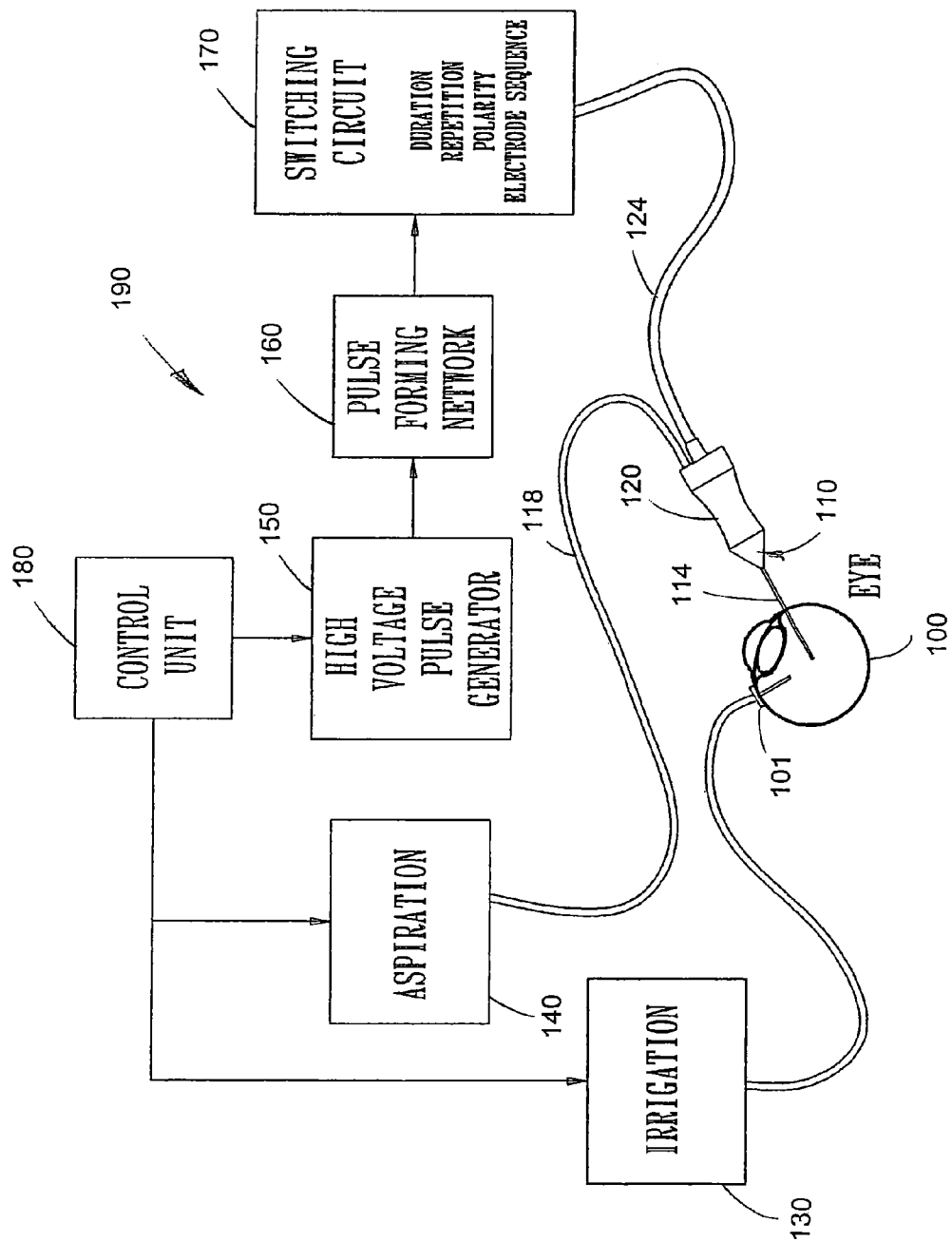
FIG. 3 is a schematic diagram of a preferred embodiment of the disclosed system.

The disclosed exemplary application of the system described herein is for the treatment of pathologic retinal conditions whereby, as shown in FIG. 1, a hollow probe 114, as described herein, using a handle 120 is inserted by a surgeon into the posterior region of the eye 100 via a pars plana approach 101, as shown in FIG. 3. Using standard visualization process, vitreous and/or intraocular membranes and tissues would be engaged by the tip 112 of the hollow probe 114, irrigation 130 and aspiration 140 mechanisms would be activated, and ultrashort high-intensity pulsed electric power from a high voltage pulse generator 150 would be delivered through a pulse-forming network 160, switching circuit 170, and cable 124, creating a disruptive high-intensity ultrashort-pulsed electrical field within the entrained volume of tissue. The adhesive mechanisms of the entrained constituents of the tissue that are drawn toward the probe tip 112 via aspiration through an aspiration line 118 connected to an aspiration lumen 122 in the hollow probe 114 would be dissociated, and the fluidic techniques employed would remove the disrupted tissue. Engagement may be axial to or lateral to the tip 112 of the hollow probe 114. Extracted tissue would be removed through the aspiration lumen 122 via a saline aspiration carrier to a distally located collection module.

All of the posterior vitreous tissue could be removed, or just specific detachments of vitreous tissue from the retina or other intraocular tissues or membranes could be realized.

Engagement disruption and removal of vitreous tissue, vitreoretinal membranes, and fibrovascular membranes from the posterior cavity of the eye and surfaces of the retina are the critical processes pursued by vitreoretinal specialists, in order to surgically treat sight-threatening conditions, such as diabetic retinopathy, retinal detachment, proliferative vitreoretinopathy, traction of modalities, penetrating trauma, epimacular membranes, and other retinopathologies.

Though intended for posterior intraocular surgery involving the vitreous and retina, it can be appreciated that the device and modality described herein is applicable to anterior ophthalmic treatments as well, including traction reduction (partial vitrectomy); micelle adhesion reduction; trabecular meshwork disruption, manipulation, reorganization, and/or stimulation; trabeculoplasty to treat chronic glaucoma; Schlemm's Canal manipulation, removal of residual lens epithelium, and removal of tissue trailers. Applicability of the disclosed apparatus and method to other medical treatments will become obvious to one skilled in the art.

PARTS OF SYSTEM

Control Unit (180)
Pulse Power Generator (150)
Pulse-Forming Network (160)
Switching Circuit (170)
Transmission Line (124)
Multi-Electrode Surgical Probe Assembly (110)
Fluidics System (130, 140)

The apparatus and method of the disclosed invention deliver pulsed high-intensity and ultrashort duration electrical field (low energy) at a pulse duration, repetition rate, pulse pattern, and pulse train length tuned to the properties of the components of the intraocular extracellular matrix (ECM). The pulse power generator 150 for the system 190 delivers pulsed DC or gated AC against a low impedance of vitreous and the irrigating solution. Included in the system 190 are energy storage, pulse shaping, transmission, and load-matching components. The peak output voltage of the high voltage generator 150 is sufficient to deliver up to a 300 kV/cm field strength using the electrodes 116 at the distal end 112 of the hollow surgical probe 114. Pulse duration would be short relative to the dielectric relaxation time of protein complexes. Also, pulse duration, repetition rate, and pulse train length (i.e., duty cycle) are chosen to avoid the development of thermal effects ("cold" process). The system 190 generates and delivers square-shaped pulses with a fast (<5 nanoseconds) rise time and fall time. In the apparatus and method disclosed herein, pulse durations would be in the nanosecond range, and the voltage would be greater than one (1) kV and preferably in the range of tens (10s) of kV.

A switching circuit 170 is incorporated to control pulse duration, repetition rate, and generate a stepwise continual change in the direction of the electrical field by switching between electrodes, reversing polarity between electrodes or a combination of both in an array of electrodes at the tip 112 of the hollow probe 114, thus creating disorder in the electric field without causing dielectric breakdown of the carrier fluid between the electrodes or thermal effects.

Paramount to the effectiveness of the disclosed invention is the choice of energy. The object is to create disorder among electrons in the outer shell of macromolecules associated with non-covalent bonds binding proteinaceous complexes together. The preferable form of energy is electricity—energizing electrons by the direct creation of an electrical field. Sources of energy, such as microwaves, laser, and ultrasound, which utilize photons and phonons to energize electrons may also be used to create the desired disorder among the electrons in the outer shell of macromolecules.

The disclosed apparatus includes a transmission line 124 and a hollow surgical probe 114 which delivers, channels, and distributes the applied energy in such a fashion as to create a confined, localized region of electrical force within a macroscopic volume of the extracellular matrix ECM (e.g., vitreous and intraocular membranes). The electrical field is presented essentially perpendicularly or orthogonally to the direction of carrier fluid movement (i.e., proteinaceous material in a water solution). FIGS. 4A, 4B, 4C, 4D, and 4E illustrate several possible electrode array embodiments at the distal end 112 of the surgical probe 114.

Figure 4A:
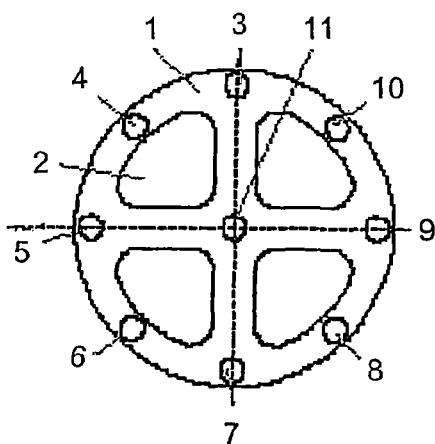
Figure 4B:
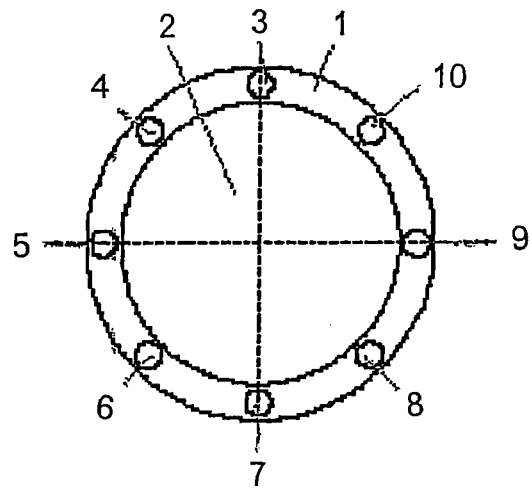
Figure 4C:
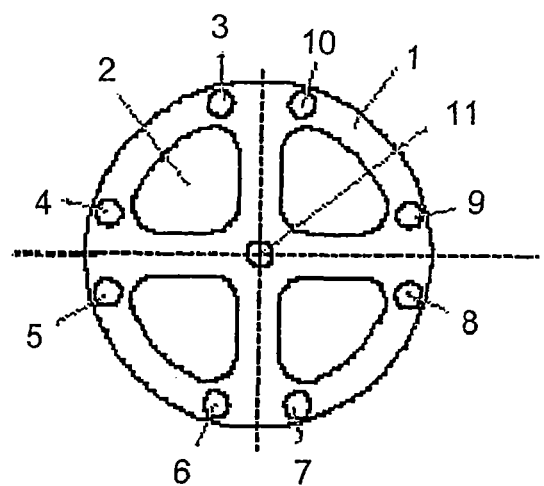
Figure 4D:
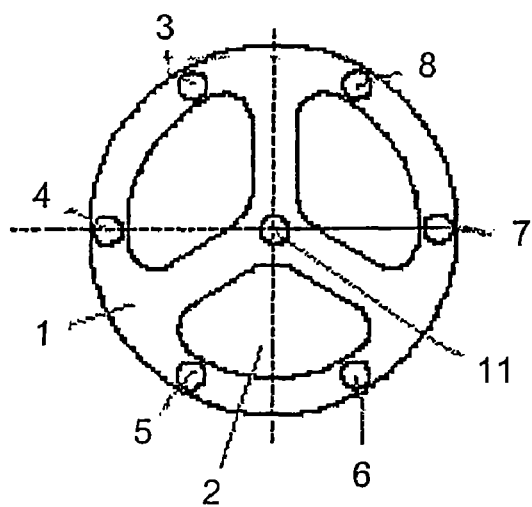
Figure 4E:
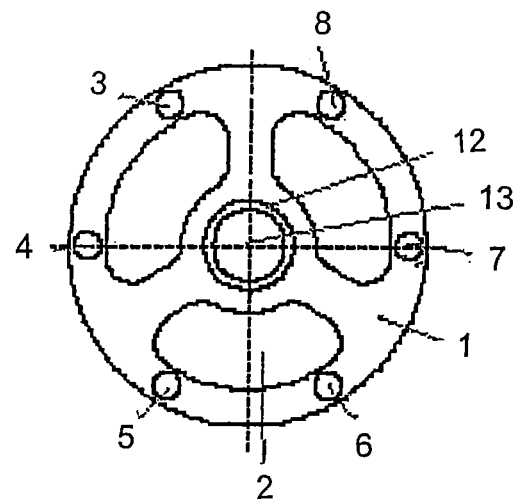

For example, reference number 1 is used in FIGS. 4A, 4B, 4C, 4D, and 4E to refer to a polymer extrusion with one or more through lumens. Reference number 2 designates the lumen for aspirated fluid flow. Reference numbers 3, 4, 5, 6, 7, 8, 9, and 10 refer to the electrode wires embedded in extrusion 1. In FIGS. 4A, 4C, and 4D, a centrally located electrode wire 11 is used. In FIG. 4E, a centrally located tubular electrode 12 is used. Also in FIG. 4E, a centrally located lumen 13 is used for fiberoptic equipment or some other form of instrumentation. Those of ordinary skill in the art will understand that numerous other configurations are possible to generate the desired pulsed rapid strong electrical field pattern. Though shown in a substantially planar fashion, the distal face of each electrode 116 may be axially staggered or aligned and may be either inset or protruding, or a combination of both, from the distal end 112 of the hollow probe 114. Though shown terminating in a plane perpendicular to the axial direction of the probe shaft, the electrodes 116 may terminate axially about a lateral window (not shown).

In the preferred embodiment, the outside diameter of the extrusion 1 is less than 0.040 inches. It is envisioned that vitreous or intraocular tissue material would be drawn toward and into the aspiration channel(s), and, as the material approached the region orthogonal to the electrodes 116, the electrodes would be activated, creating an ultrashort, high-intensity disruptive electric field between electrodes 116.

Variable field projections with constantly changing direction would result from the placement and sequential activation of arrays of electrodes. Tables 5A, 5B, 5C, 5D, and 5E illustrate a plan of electrode activation for the embodiments shown in FIGS. 4A, 4B, 4C, 4D, and 4E, respectively. In Table 5A, there are 12 pulses that are illustrative of a pulse sequence used on the embodiment of the end of the probe 114 shown in FIG. 4A. The first pulse utilizes the electrode 116, given reference number 11, as an anode, and the cathodes are 3, 4, 5. The second pulse is just the opposite. The remaining pulses are illustrative of a pulse arrangement to establish a variable direction electrical filed.

In Table 5B, there are 11 pulses that are illustrative of a pulse sequence used on the embodiment of the probe 114 shown in FIG. 4B.

In Table 5C, a 12-pulse sequence is shown as in FIG. 5A for use on the probe shown in FIG. 4C.

In Tables 5D and 5E, a 10-pulse sequence is shown for the probes shown in FIGS. 4D and 4E, respectively. Numerous other field patterns are envisioned, depending on the embodiment and the sequence of electrode activation. The object of the electrode activation is to utilize the polar properties of water and protein, create disorder with rapidly changing high-intensity electric field direction, and thus induce conformal changes of both water and protein, leading to momentary tissue dissociation. The dissociated tissue complex localized within the region of applied electrical field is then removed using concurrent fluidic techniques before the transient effects of the assault expire (relax).

In the case of embodiment 4E, the central electrode 12 may be a tubular conductive electrode with a center region 13. The central region 13 could be a through lumen for an irrigation or instrument channel, or the central region could be a fiber-optic device for delivery of light.

As previously stated, the position of electrodes in the arrays and the number of electrodes may be configured to present the most efficacious disruptive electric fields. The electrodes may also be axially positioned so that one or more of the electrodes does not terminate at the same length or same axial position. The terminal end of the electrodes may be shaped in such a fashion as to optimize spatial field strength between the electrodes. Shapes of the terminal end of the electrodes may include straight edges, corners, sharps, curvatures (constant and variable) or combinations thereof chosen to project and optimize electric field strength distribution between the electrodes.

Fluidic techniques (aspiration) are included to draw in and remove the dissociated tissue volume before reassembly of non-covalent proteinaceous relationships can occur. The fluidic techniques used in the preferred embodiment include both saline irrigation and effluent aspiration. In the preferred embodiment, the fluidics system includes irrigation and aspiration features which are uniquely matched such that the volume and pressure within the eye are maintained within physiological limits. The posterior vitreous contains more than 97% water, and an important function of the fluidics system is to ensure dilution, hydration and stable impedance of engaged material. In the preferred embodiment, the aspiration channel is incorporated into the hollow surgical probe 114 such that intraocular tissues are drawn into the aspiration lumen 122 or channels while being subjected to the disruptive electric field described above. The volume flow rate of the aspirated effluent is matched to the dissociation rate of the hydrated proteinaceous material under the influence of the disruptive electric field. It is anticipated that irrigation with BSS® irrigating solution or BSS PLUS® irrigating solution, both available from Alcon Laboratories, Inc., will be utilized. Innocuous properties and ingredients may be incorporated into the irrigation fluid to enhance dissociation. The irrigation route/channel may be incorporated into the surgical probe, as illustrated in FIG. 4E, it may be provided in an independent cannula, or it may be provided by a combination of both means.

FIG. 6 is a perspective of an alternate embodiment of a probe assembly 210 including three electrodes. As in the preferred embodiment 110, the probe assembly 210 includes a hollow probe 214 and a handle 220. Tissue would be engaged by the tip 212 of the hollow probe 214. A better understanding of probe assembly 210 may be had by reference to FIGS. 6, 7, and 8. The three electrodes 216 are positioned at substantially equal angular intervals around a central spine 217 within the probe 214. Between the electrodes 216 are the irrigation channels 215. In the center of the central spine 217 is located an aspiration lumen 222. Covering the central spine 217, the irrigation channels 215, and the electrodes is an external jacket 219 which terminates in an atraumatic tip 221. The probe assembly 210 is positioned so that the tissue to be removed is located just inside the atraumatic tip 221.

The support system 290 for probe assembly 210, shown in FIG. 10, is similar to that of the preferred embodiment shown in FIG. 3 but for the inclusion of a probe tip irrigation system 235. Included is a global irrigation system 230, an aspiration system 240 connected to an aspiration line 218, a control unit 280, one or more high-voltage pulse generators 250, a switching circuit 270 connected to a transmission line 224, and a probe tip diluting irrigation system 235 connected to a probe tip irrigation tube 237.

As in FIGS. 4A, 4B, 4C, 4D, and 4E which display the electrodes at the probe tip, FIGS. 11A and 11B illustrate alternate arrangements of electrodes 1, 2, 3, and 4 in the probe assembly 210. FIGS. 12A and 12B correspond to FIGS. 11A and 11B showing exemplary sequences of electrode activation to create the non-plasma, non-contact energized disruptive region around the proteinaceous tissue. To better understand the creation of this non-plasma, non-contact energized disruptive region, FIGS. 13A and 13B illustrate the field lines for the sequence of pulses illustrated in FIGS. 12A and 12B, respectively, where the polarity of the electrodes is not reversed.

FIG. 14 is a schematic diagram of the three-channel pulse generator 250 which controls the duration of individual pulses, the repetition rate of the individual pulses, and the pulse length of the pulse train.

FIG. 15 is a table illustrating the channel states of an exemplary single cycle of pulsing of the three-channel pulse generator 250 shown in FIG. 14.

A still better understanding of the system 290, shown in FIG. 10, may be had by understanding that the probe assembly 210 includes a plurality of through lumens 215 for supplemental irrigation, as shown in FIGS. 6, 7, 8, and 9, respectively. The flow rate of irrigation is less than the aspiration rate through the central lumen 222, such that the escape velocity of the supplemental irrigation fluid is less than the entrance velocity of diluted hydrated intraocular tissue. Additional irrigation fluid is presented by probe tip diluting irrigation mechanism 235 which is external to the probe (FIG. 10). The irrigation fluid is used both to dilute intraocular tissue and to maintain a stable or near constant impedance between the electrodes 216, thereby avoiding significant shifts in realized energy delivery and field strength. Properties of the irrigation fluid such as pH and ingredients may be chosen to enhance vitreous dissociation.

A third conduit for irrigation 237 connects the probe assembly 210 to the supplemental irrigation source 235. Also to be noted, in FIG. 10, the pulse forming network is incorporated into the high voltage pulse generator 250.

By reference to FIGS. 11A and 12A, it may be seen that, in lieu of reversing polarity of the electrodes 216 between pulses, the active anodes and cathodes are switched between the electrodes. The field lines created are shown in FIG. 13A to illustrate an example of an electric field for each pulse. For the three electrode 1, 2, and 3 configuration, shown in FIG. 11A, a single cycle includes three pulses emanating from different directions. In the table at FIG. 12A, sequencing examples are shown for cases involving electrode switching and not actual polarity (reversal). The table at FIG. 12B and the field lines shown in FIG. 13B illustrate the possible four-electrode embodiment 1, 2, 3, and 4, shown in FIG. 11B, where the electrodes act in pairs as anodes and cathodes.

The three-channel pulse generator, whose schematic is illustrated in FIG. 14, shows that the triggering of one channel sends a pulse to an electrode, then triggers a second channel which, in turn, sends a pulse to a different electrode, then triggers the third channel which, in turn, sends a pulse to a different electrode and triggers the first channel to start the sequence over again. As one channel fires a pulse, the other two channels offer zero resistance and act as return circuits for the fired pulse. The sequencing of channels may be ordered, or it may be random.

FIG. 15 illustrates the polarity condition of each channel during a pulse firing. The polarity condition of each channel results from electrode switching as opposed to actual polarity switching on any single channel.

A further embodiment of probe assembly 210 is pictured in FIGS. 16-23. FIGS. 16-19 depict an embodiment with electrodes 216 that are flattened and axially elongated. These electrodes 216 are flattened with the large flat portion aligned radially with respect to the aspiration channel 222. The sharp corners of electrodes 216 allow for a more intensely focused electric field to be produced at the aspiration channel 222. These electrodes 216 terminate at the orifice of jacket 219.

FIGS. 20-23 depict an embodiment with electrodes 216 that have pointed tips. These electrodes 216 are flattened with the large flat portion aligned radially with respect to the aspiration channel 222. These electrodes 216 terminate in a folded pointed tip with the pints directed radially inward toward the aspiration channel 222. The sharp corners of electrodes 216 allow for a more intensely focused electric field to be produced at the aspiration channel 222.

In the two embodiments depicted in FIGS. 16-23, the three electrodes 216 are positioned at substantially equal angular intervals around a central spine 217 within the probe 214. Between the electrodes 216 are the irrigation channels 215. In the center of the central spine 217 is located an aspiration lumen 222. Covering the central spine 217, the irrigation channels 215, and the electrodes is an external jacket 219 which terminates in an atraumatic tip 221. The probe assembly 210 is positioned so that the tissue to be removed is located just inside the atraumatic tip 221. In FIGS. 17, 19, 21, and 23, an opening 227 between the jacket 219 and the aspiration channel 222 allows irrigation fluid to pass in a waterfall effect near the electrodes 216.

The operation of the probe assembly of FIGS. 16-23 is similar to that depicted in FIGS. 11A, 12A, and 13A. Other modes of operation previously described are also appropriate with the assembly of FIGS. 16-23.

The disclosed system provides the following advantages:

a) Traction-free removal of intraocular tissues from the posterior segment of the eye.

b) Manageable dissociation of small volumes of tissue with no far-field effect.

Specifically, there is no far-field migration, leakage, or scattering of the electrical field. Unlike enzymatic processes which affect the entire posterior of the eye, including the retina, the effect of the disclosed CHIP EFFF is localized.

c) Partial vitrectomy or traction release without total vitrectomy.

Most vitreoretinal surgical applications required extraction of all the vitreous in the posterior of the eye. Using the disclosed system, it is possible to selectively detach proteinaceous tissue and collagen from the retinal membrane without removing all the vitreous. Accordingly, the need for post-surgical artificial vitreous is eliminated.

d) No reactive oxygen species is created.

As opposed to ablative technologies, such as lasers, plasmas, and thermal-generating modalities, the disclosed system affects only the non-covalent adhesion aspects of the vitreous and intraocular membranes; therefore, no toxic chemicals or ROS are induced or released. Insufficient energy is delivered to cause thermal events.

e) Safety.

Discontinuation of energy delivery results in reassembly of proteinaceous tissue. Thus, the disclosed method can be discontinued almost instantaneously at any time without permanent damage to target tissue.

f) Multimodal (extract, coagulate, cut, stimulate).

Since the probe has a plurality of electrodes, it is possible to change power settings to achieve different functional results. In the CHIP EFFF mode, the probe would be utilized to extract vitreous and intraocular membranes. In the coagulator mode, RF energy could be applied in order to stop vascular hemorrhage. In a cut mode, RF energy at the appropriate power and frequency could be applied as to actually create a plasma or spark erosion to effect cutting of tissue. In the stimulate mode, an electrical pulse of lower power could be delivered for therapeutic purposes.

g) Reduction in instrument exchange.

In posterior ocular surgery, an abundant number of custom and specialized instruments are required to engage, tease, separate, and remove vitreous and intraocular membranous material. Instrument exchange during surgery is a major factor in post-operation complications. Use of this disclosed invention renders many prior-art instruments obsolete and minimizes instrument exchange.

h) No moving parts.

Reduction in cost and labor for probe fabrication is realized. Fabrication of mechanical vitrectomy probes is labor-intensive. The disposable hollow probe perceived herein consists of a small handle with an attached multi-lumen co-extrusion or assemblies with wires in the lumens or crevices. Skill in assembly compared to current mechanical assemblies is reduced.

i) Posterior and anterior applications.

While designed for tractionless removal of vitreous and intraocular tissues, the disclosed apparatus may be utilized for certain anterior segment surgeries, such as trabecular meshwork stimulation, removal of residual lens epithelium, and removal of tissue trailers, anterior vitrectomy, among others.

j) Hybrid-friendly.

The simplicity of design in the disclosed probe assembly makes it useful as stand-alone or an adjunct to other tissue disruption and extraction means, such as mechanical vitrectomy, AquaLase® surgical instruments, available from Alcon Laboratories, Inc., and chemical vitrectomy (enzymatic action).

While the disclosed invention has been described in terms of its preferred and alternate embodiments, those of ordinary skill in the art will realize that still other embodiments have been enabled by the foregoing disclosure.

What is claimed is:

1. A method of using a high-intensity pulsed electric field to increase the fluidity of a volume of ocular tissue, the method comprising:
   (a) providing a volume of ocular tissue having protein bonds; and
   (b) applying a localized pulsed electric field to the ocular tissue without causing an electron avalanche; wherein the localized pulsed electric field is generated by applying to the ocular tissue a series of electric pulses, the series of electric pulses having a pulse duration shorter than a dielectric relaxation time of the protein bonds and having an electric field strength greater than one KV/cm and up to 300 KV/cm; and further wherein the series of electric pulses is delivered to the ocular tissue by two or more electrodes such that said applying of the series of electric pulses increases the fluidity of the ocular tissue by dissociating the protein bonds.

2. The method of claim 1, further comprising:
changing a shape of a pulse in the series of electric pulses.

3. The method of claim 1, further comprising:
changing a width of a pulse in the series of electric pulses.

4. The method of claim 1, further comprising:
changing a rise time of a pulse in the series of electric pulses.

5. The method of claim 1, further comprising:
changing a fall time of a pulse in the series of electric pulses.

6. The method of claim 1, further comprising:
changing a pulse repetition rate in the series of electric pulses.

7. The method of claim 1, further comprising:
changing a number of pulses in the series of electric pulses.

8. The method of claim 1, further comprising changing a pulse-train repetition-rate in the series of electric pulses.

9. The method of claim 1, further comprising:
changing a pattern of the pulses in the series of electric pulses.

10. The method of claim 1, further comprising:
changing an amplitude of a pulse in the series of electric pulses.

11. The method of claim 1, further comprising:
changing a number of pulse-trains in the series of electric pulses delivered to the ocular tissue.

12. The method of claim 1, further comprising:
changing a polarity of a pulse in the series of electric pulses.

13. The method of claim 1, wherein the two or more electrodes are arranged in an array and wherein the series of electric pulses is delivered by providing electrical switching of each electric pulse between the two or more electrodes.

14. The method of claim 1, wherein the electrical switching changes a number of electrodes which are activated in the array.

15. The method of claim 14, further comprising:
changing an activation sequence of the active electrodes.

16. The method of claim 1, further comprising:
changing a direction of the electric field.

17. The method of claim 1, further comprising:
changing a polarity of the electric field.

18. The method of claim 1, wherein the pulses have squarish or trapezoidal shape.

19. The method of claim 1, wherein the pulse duration in the series of electric pulses is in the sub-microsecond range.

20. The method of claim 1, wherein a pulse-rise-time in the series of electric pulses is shorter than 5 nanoseconds.

21. The method of claim 1, wherein a pulse-fall-time in the series of electric pulses is shorter than 5 nanoseconds.

* * * * *